United States Patent [19]
Epstein et al.

[11] Patent Number: 6,063,055
[45] Date of Patent: May 16, 2000

[54] TURBULENCE MIXING HEAD FOR A TISSUE SEALANT APPLICATOR AND SPRAY HEAD FOR SAME

[75] Inventors: Gordon Howard Epstein, Freemont; Alan Kirby Plyley; Russell James Redmond, both of Goleta, all of Calif.

[73] Assignee: Biosurgical Corporation, Pleasanton, Calif.

[21] Appl. No.: 09/037,160

[22] Filed: Mar. 9, 1998

Related U.S. Application Data

[63] Continuation-in-part of application No. 08/838,078, Apr. 14, 1997, and a continuation-in-part of application No. 08/839,614, Apr. 14, 1997, Pat. No. 5,971,956, and a continuation-in-part of application No. 08/946,364, Oct. 7, 1997.

[51] Int. Cl.$^7$ .................................................. A61M 5/00
[52] U.S. Cl. ............................................. 604/82; 604/191
[58] Field of Search ................... 604/82, 73, 94, 604/131, 134, 135, 173, 181, 187, 191, 200, 214, 218, 224, 228, 46, 49, 56; 424/423; 222/387, 340; 251/322; 137/625.4

[56] References Cited

U.S. PATENT DOCUMENTS

| | | | |
|---|---|---|---|
| 3,159,312 | 12/1964 | Sciver, II | 222/137 |
| 4,040,420 | 8/1977 | Speer | 604/82 |
| 4,735,616 | 4/1988 | Eibl et al. | 604/191 |
| 4,874,368 | 10/1989 | Miller et al. | 604/82 |
| 5,116,315 | 5/1992 | Capozzi et al. | 604/82 |
| 5,474,540 | 12/1995 | Miller et al. | 604/191 |

*Primary Examiner*—John D. Yasko
*Attorney, Agent, or Firm*—Handal & Morofsky

[57] ABSTRACT

The invention provides a handheld, manually operable fluid applicator, particularly suited to the needs of surgeons, for dispensing a multi-component fluid applicator, for example fibrin and thrombin components of a tissue adhesive. The sealant components undergo turbulent mixing in a mixing chamber which causes a sharp change of at least 60 degrees in the direction of flow of each sealant component, to provide effective mixing and a quality sealant product. The mixing chamber has an increased cross-sectional area over the combined areas of the component supply passages and the fluid flows are directly opposed to impinge on each other in the mixing chamber. The mixing chamber is incorporated in a novel one-piece flexible and resilient manifold. Dual nozzle spray applicators with poppet valves are also disclosed.

19 Claims, 14 Drawing Sheets

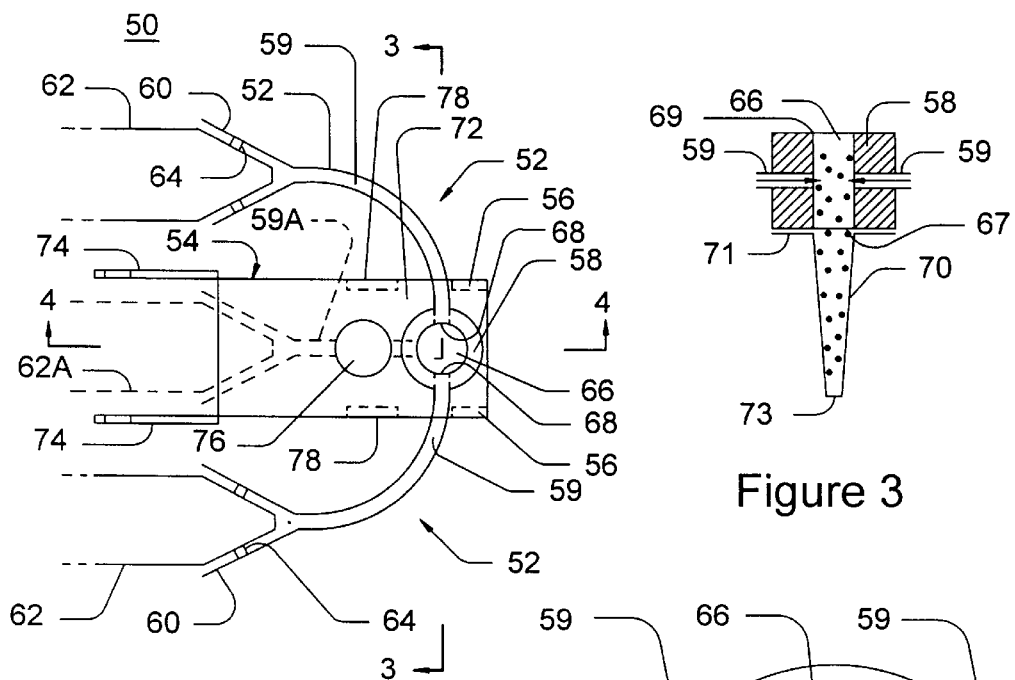
Figure 2
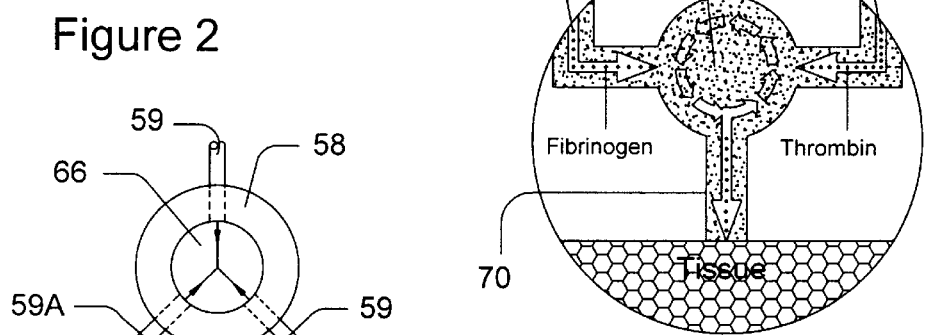
Figure 3
Figure 3A
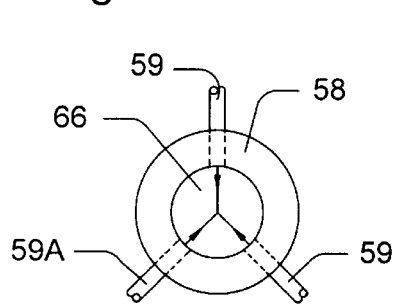
Figure 3B
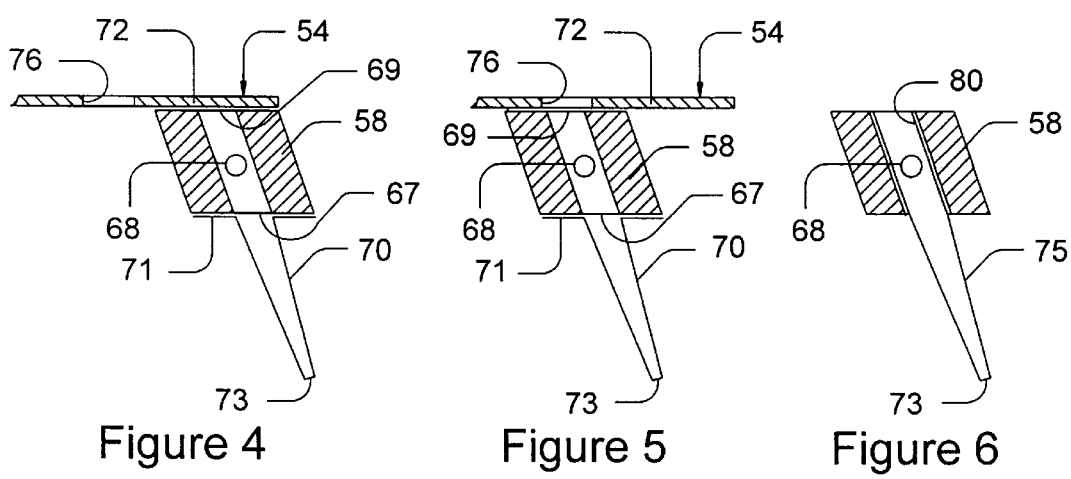
Figure 4      Figure 5      Figure 6

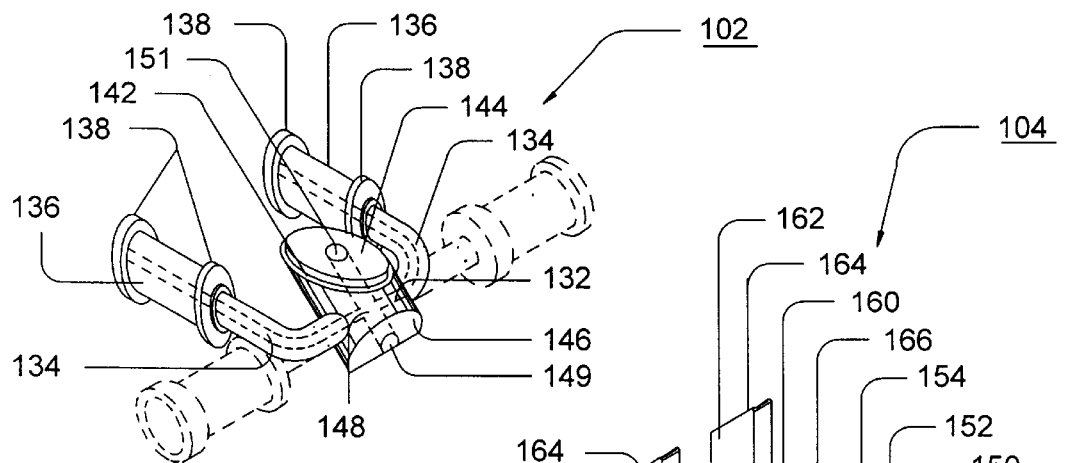
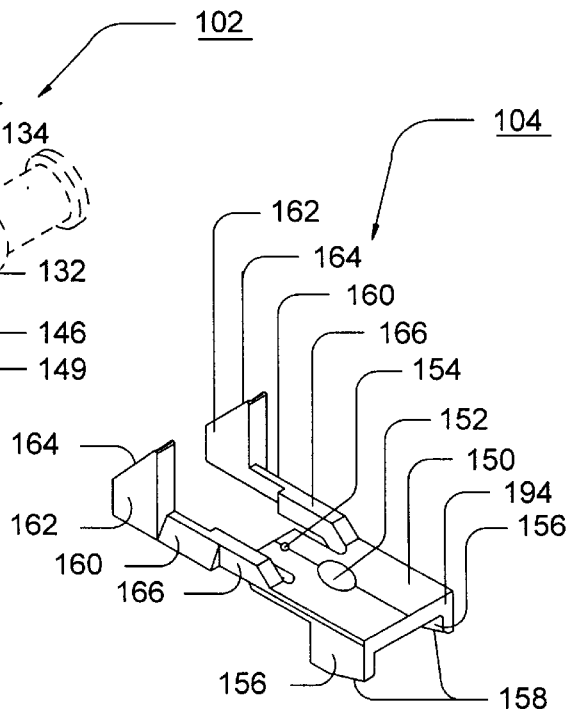
Figure 8
Figure 9
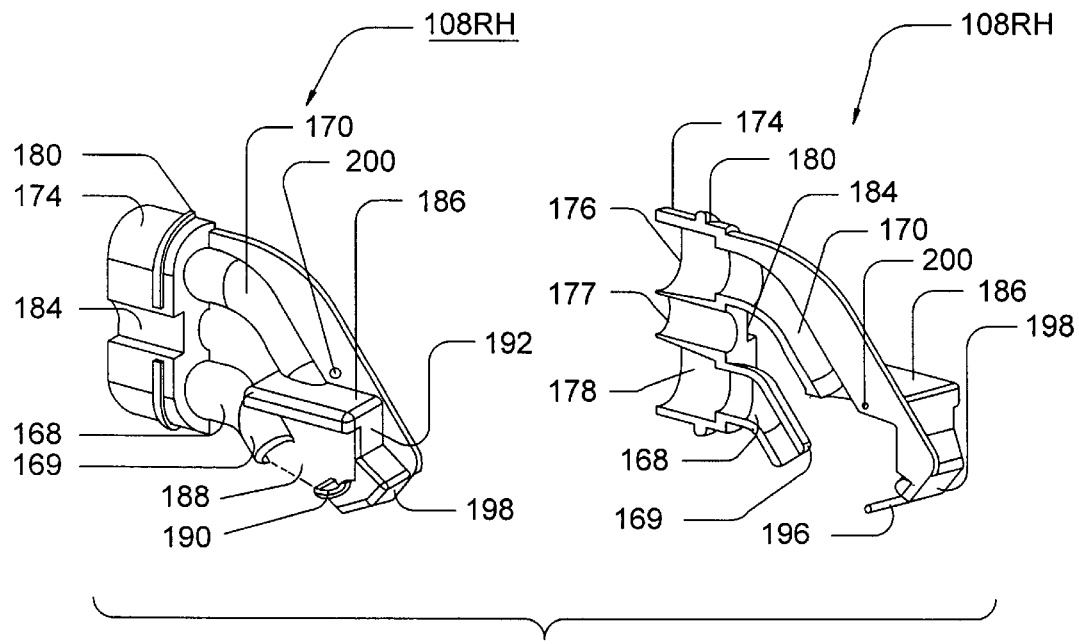
Figure 10

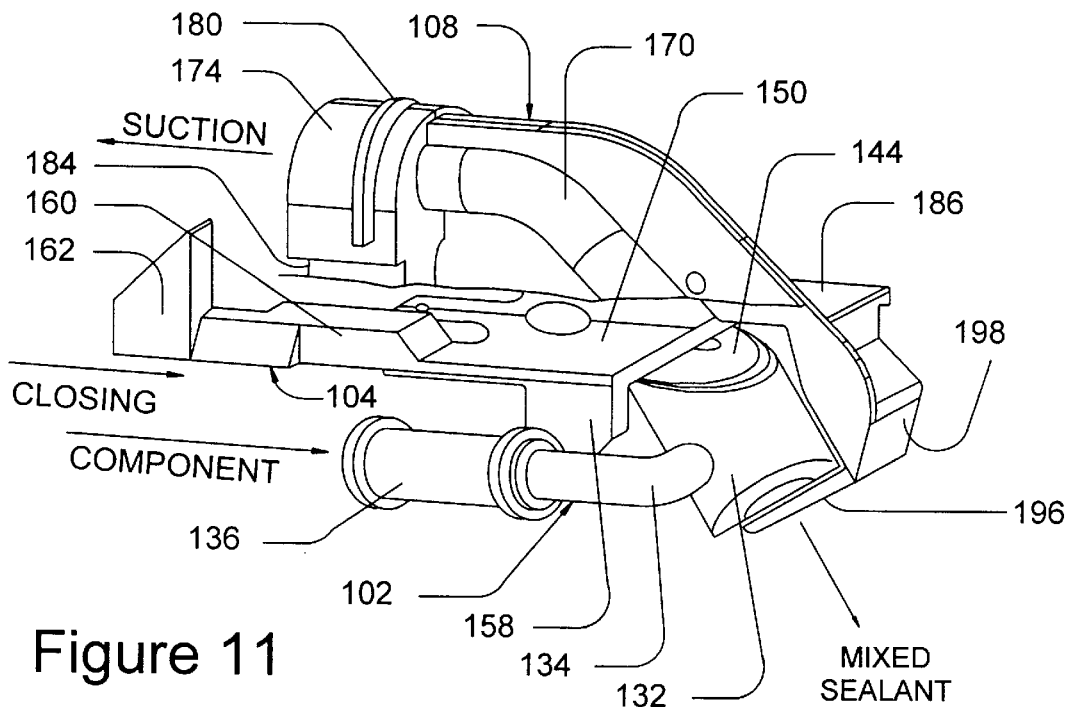
Figure 11
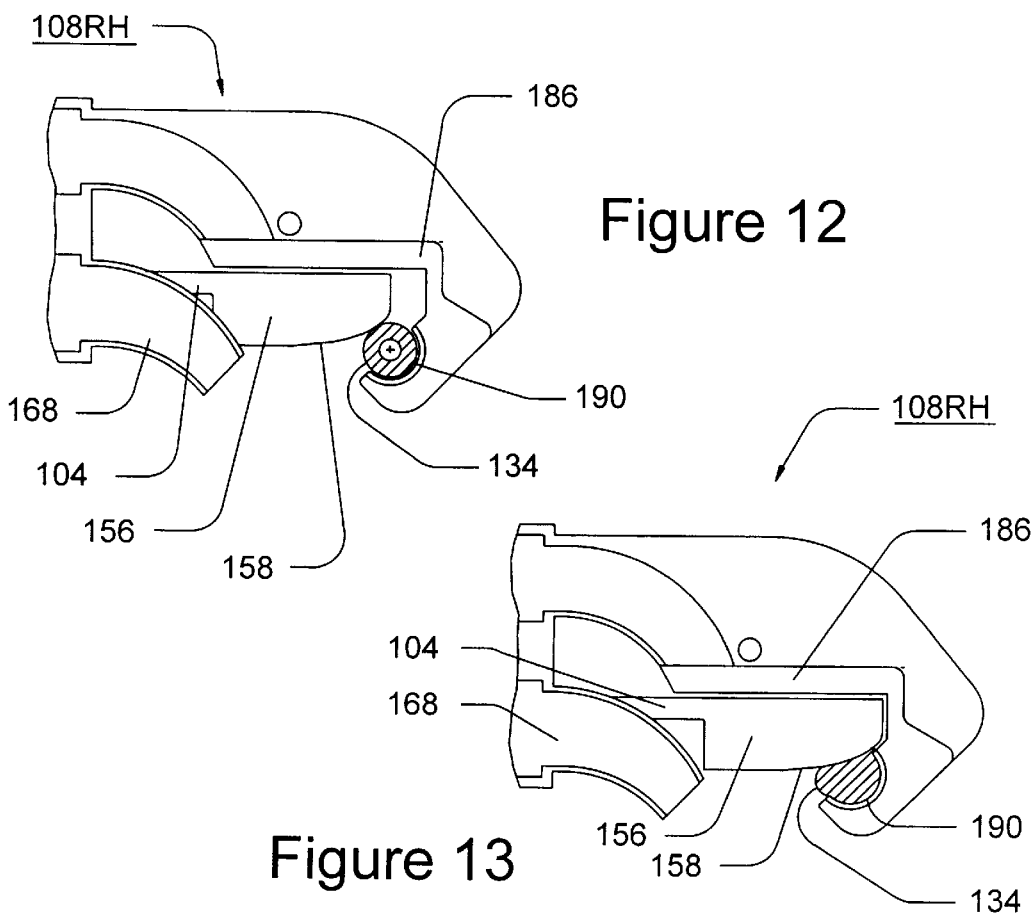
Figure 12
Figure 13

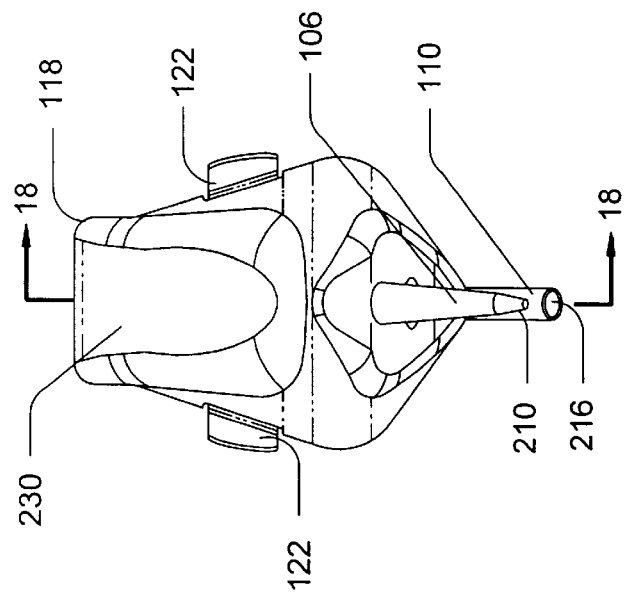
Figure 16
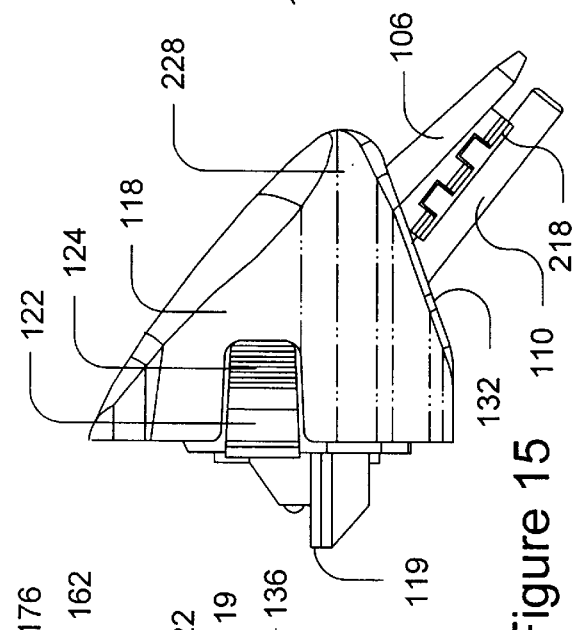
Figure 15
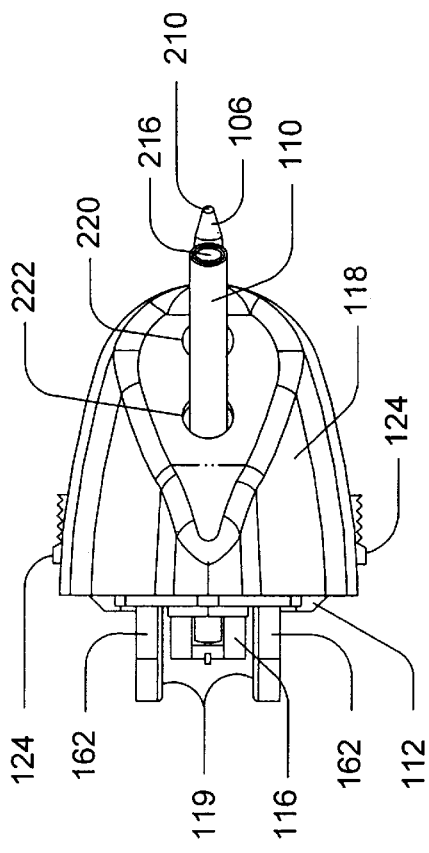
Figure 17
Figure 14

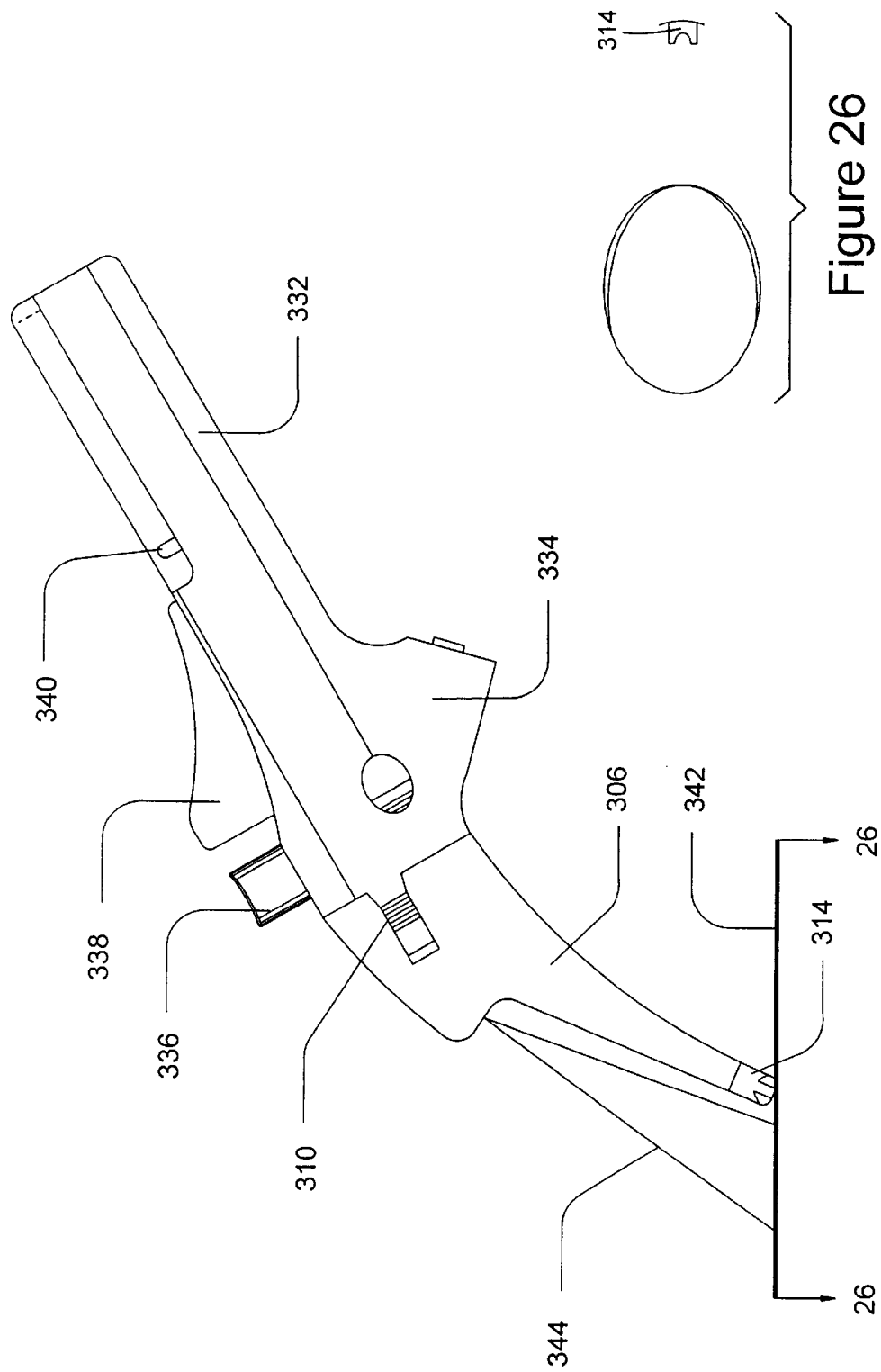

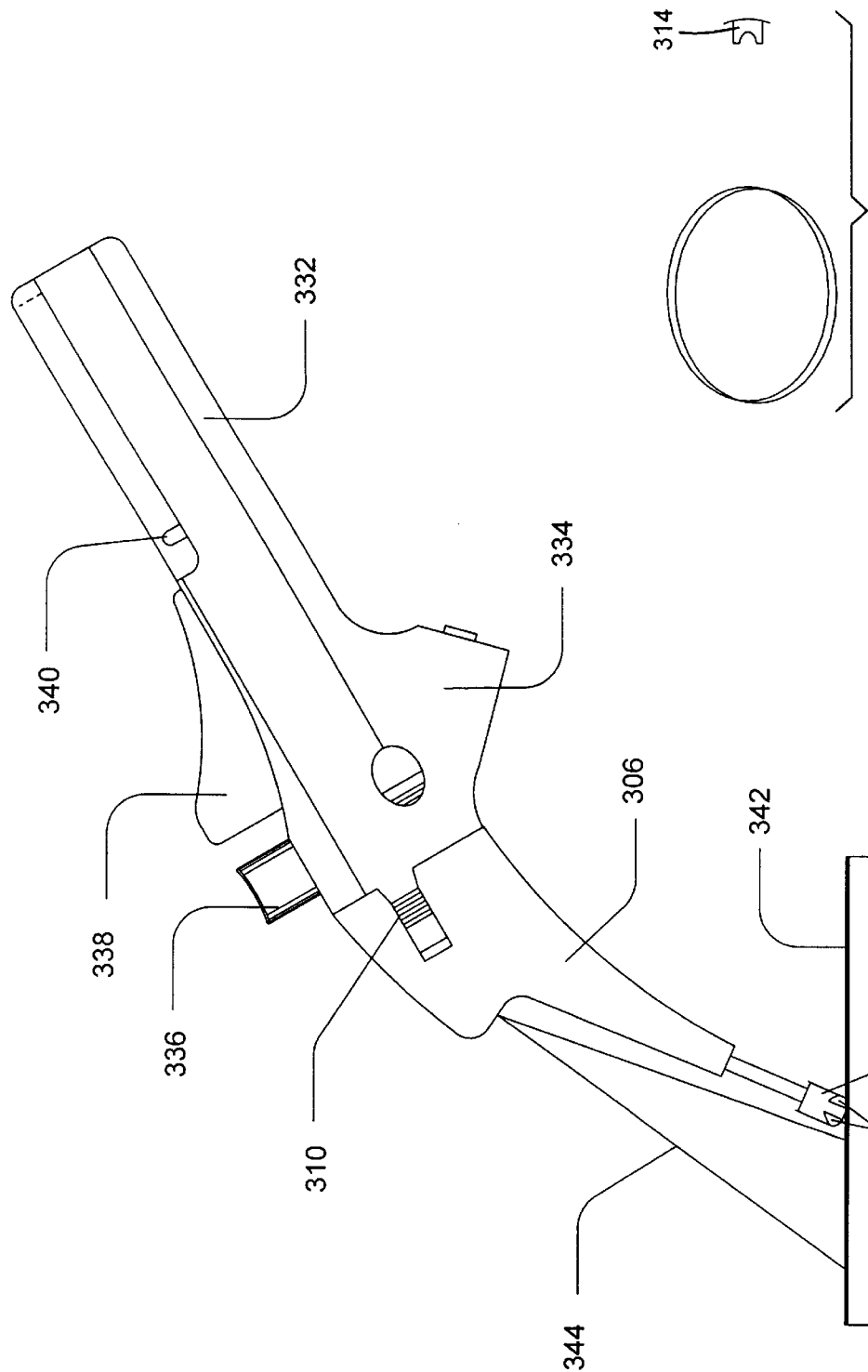

2

TURBULENCE MIXING HEAD FOR A TISSUE SEALANT APPLICATOR AND SPRAY HEAD FOR SAME

CROSS-REFERENCE TO RELATED APPLICATIONS

This application is a continuation-in-part of our U.S. patent applications Ser. No. 08/838,078 and Ser. No. 08/839,614, now, U.S. Pat. No. 5,971,956 both filed Apr. 14, 1997, of application Ser. No. 08/946,364 pending filed Oct. 7, 1997. The disclosures of the aforementioned United States patent applications, "the parent applications" are hereby incorporated herein by reference thereto.

BACKGROUND OF THE INVENTION

1. Field of the Invention

The present invention relates to handheld fluid applicators, wherein an operator operates a fluid dispensing actuator to drive fluid from a reservoir and out of the applicator, through an applicator tip. Such applicators have many different uses and are particularly well suited for dispensing glues and adhesives and indeed are common household items for applying epoxy glues, viscous carpentry glues and caulks and so on. More specialized uses with greater performance requirements, as will be described herein, are for applying tissue adhesives in a surgical context to repair tissues damage, and for equivalent professional, medical, veterinary or biological uses.

2. Description of Related Art Including Information Disclosed under 37 CFR 1.97 and 37 CFR 1.98

Most prior art tissue sealant systems dispense side-by-side streams of tissue sealant components because of the problems of clogging which are associated with devices that provide internal mixing of the components. While some kown devices provide internal mixing, they have the drawback of producing an inferior sealant product.

SUMMARY OF THE INVENTION

The invention solves a problem. It solves the problem of providing a fluid applicator mixing head which can provide rapid internal mixing while avoiding problems of clogging.

In a preferred embodiment, the present invention solves this problem by providing a mixing head for a sealant applicator which uses apposite flow wherein multiple adhesive component fluids are discharged into a mixing chamber in directions such as to provide directly opposed flow components in the mixing chamber, e.g. directly opposite to one another, thereby to cause turbulence and active mixing of the adhesive fluid components prior to discharge from the dispenser. Employing a quick setting component adhesive, such for example as the fibrin adhesives used in surgery, curing and resultant setting or viscosity increase may be initiated, or occur, within the dispenser prior to discharge, providing a more viscous flow out of the dispenser than would be obtained without apposite mixing.

BRIEF DESCRIPTION OF THE DRAWINGS

One way of carrying out the invention is described in detail below with reference to the drawings which illustrate one or more specific embodiments of the invention and in which:—

FIG. 2 is a partial schematic plan view of a first embodiment of mixing head according to the invention, suitable for incorporation in an applicator tip for an applicator intended for dispensing a two-component adhesive system, such as a tissue sealant;

FIG. 3 is a section on the line 3—3 of FIG. 2;

FIG. 3A is a schematic depiction of a principle of the invention;

FIG. 3b is a partial schematic plan view of a further embodiment of mixing chamber for a mixing head according to the invention;

FIG. 4 is a section on the line 3—3 of FIG. 2 showing one position of a shuttle valve;

FIG. 5 is a view similar to FIG. 4 showing another position of the shuttle valve;

FIG. 6 is a view similar to FIG. 4, without the shuttle valve, illustrating another embodiment of the invention;

FIG. 8 is an enlarged view of a manifold being a component of the applicator tip shown in FIG. 7;

FIG. 9 is an enlarged view of a shuttle valve being a component of the applicator tip shown in FIG. 7;

FIG. 10 is an enlarged view of the two halves of a clamshell being a component of the applicator tip shown in FIG. 7;

FIG. 11 is a partially cutaway view of an assembly of some of the components shown in FIG. 7;

FIG. 12 is a schematic, partial right-hand elevation of the clamshell and shuttle valve shown in FIG. 7, with a sectional view through a manifold arm, showing a first position of the shuttle valve;

FIG. 13 is a view similar to FIG. 12 showing a second position of the shuttle valve;

FIG. 14 is a rear elevation of the applicator tip of FIG. 7, with components assembled;

FIG. 15 is a right-hand side elevational view of the assembled applicator tip as shown in FIG. 14;

FIG. 16 is a front elevational view of the assembled applicator tip as shown in FIG. 14;

FIG. 17 is a bottom plan view of the assembled applicator tip as shown in FIG. 14;

FIG. 21 is a top plan view of a spray head applicator tip according to another aspect of the invention which spray head is attachable to a sealant or other fluid applicator body to dispense multiple sprays of multiple components therefrom;

FIG. 25 is a right side elevational view of the spray head shown in FIGS. 21–24 assembled with an applicator body, showing the assembly in a first position of use;

FIG. 26 is a plan view on the line 26—26 of FIG. 25, showing one possible spray pattern at an intended work surface location;

FIG. 27 is a view similar to FIG. 25 showing the assembly in a second position of use, with its nose extended;

FIG. 28 is a plan view on the line 28—28 of FIG. 27, showing one possible spray pattern, at an intended work surface location, with the extended nose configuration of spray head shown;

DESCRIPTION OF THE PREFERRED EMBODIMENTS

Figure 1:
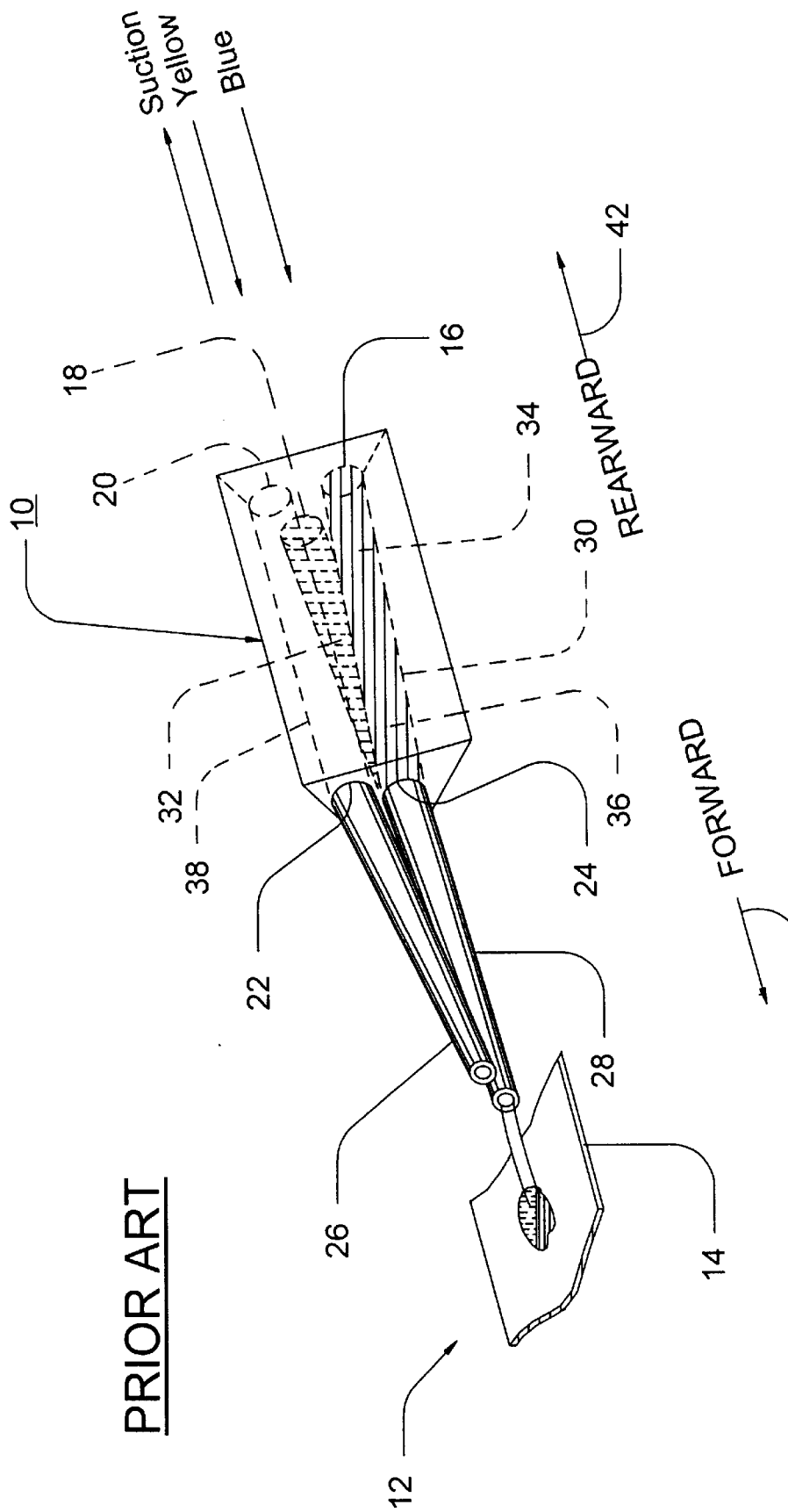
FIG. 1 is a partial schematic perspective view of a prior art embodiment of mixing head for a tissue adhesive applicator.

The structure of mixing head 10 shown in FIG. 1 of the accompanying drawings corresponds essentially with FIG. 6A of Epstein U.S. Pat. No. 5,226,877 ("Epstein '877" herein). In use, the mixing head 10 is detachably connected to a manually operable applicator enabling a surgeon or other user to controllably dispense dual components of a tissue sealant or adhesive, for example a fibrinogen-thrombin adhesive, through the mixing head 10. Suitable sealants comprise two liquid components that are mixed within the mixing head to provide a coagulatable mixture that clots, forming solid structures, within a time frame that varies depending upon the characteristics of the components, for example, active agent concentration, and other factors.

In FIG. 1, different reference numerals have been employed, and additions have been made to FIG. 6A of Epstein '877 to show schematically the transit of two colored fluids through the mixing head and their deposit as a pool 12 of mixed liquids on a support surface 14, which is not intended to simulate a work surface but rather is shown as collecting the dispensed mixture for visual inspection.

The prior art mixing head 10, as shown in FIG. 1, has three fluid passage ports at its rearward end, of which two, ports 16 and 18, when in practical use, are connected to the applicator to receive liquid adhesive components therefrom, while suction is applied to the third, port 20, here shown as located above and between ports 16 and 18. For illustrative purposes, the device has here been shown as admitting a blue fluid to port 16 and a yellow fluid to port 18.

Forwardly, the mixing head 10 comprises a suction-in port 22 and a mixed fluid exit port 24. The term "suction" is used herein in the sense of the direction of air flow when suction is applied, which will be from the tissue surface, or other application surface, towards a suitable source of suction to which the applicator is connected, in an operating room, or elsewhere. A suction applicator tube 26 and a single mixed adhesive applicator tube 28 are connected respectively to suction-in port 22 and mixed exit port 24. In Epstein '877 it is explained, at column 12 lines 31–38, using different reference numerals, that the suction tube 26 is shorter than adhesive tube 28 so that the suction tube 26 does not interfere visually or functionally with the application of the adhesive. Furthermore, the patent explains that materials from the site of application, when suctioned are brought along the exterior surface of the adhesive channel 28 to the orifice of the suction channel 26 and that this action provides gentle, a traumatic suction required in microsurgery.

The interior of the mixing head 10 has a Y-shaped channel 30 which connects the two fluid entry ports 16 and 18 with the mixed adhesive exit port 24. Y-shaped channel 30 comprises separate limbs 32, 34 leading from liquid entry ports 16 and 18. respectively, and provides an impingement zone 36 at the base of the Y, where limbs 32 and 34 merge together, which zone 36 connects with exit port 24.

A suction channel 38 connects rearward suction port 20 to forward suction-in port 22. As shown by arrows 40 and 42, and in accordance with customary usage, the forward direction is that toward the work surface, or support 14, while the rearward direction is toward the user.

When pressure is applied by the user, the blue and yellow liquids are moved through ports 16 and 18 into Y-shaped channel 30, where they mix and emerge from applicator 28 in a single stream to be deposited on surface 14, forming pool 12. While the liquids mix, in the sense of becoming combined into a single stream, prior to the present invention, it was not apparent that the stream of liquid emerging from applicator tube 28 might not comprise an intimate mixture or homogenous dispersion of the two liquids.

However, it has been discovered, pursuant to the present invention, by separately feeding colored test liquids to ports 16 and 18, for example a blue liquid to port 16 and a yellow liquid to port 18, that the liquids do not in fact mix intimately and the pool 12 of emergent liquid contains identifiable regions of blue or yellow liquid rather than being uniformly colored green as might be expected with effective mixing. Considering the apparent opportunities for commingling in the impingement zone 36, and in applicator tube 28, this result is surprising. Evidently, the configurations of Y-shaped channel 30, including the gentle angle at which the streams of liquid merge, and of applicator tube 28, are such as to provide significant laminar flow so that the two liquids retain at least some spatial separation and do not completely mix.

Such incomplete mixing can be undesirable, if it affects the performance of the sealant, affecting its time versus bonding strength parameters, performance reproducibility spatial consistency, or final bond strength. On the other hand, by reducing the extent of exposure of well mixed sealant to internal structural surfaces of the applicator, the risk of clotting with deposit of solids and consequent obstruction of flow, may be reduced.

The invention solves the problem of lack of sealant effectiveness which may occur with prior art sealant applicators, which pursuant to the present invention has been discovered to be attributable to delivery to the work site of incompletely mixed tissue sealant components. To this end, the invention provides a mixing head for a tissue sealant applicator which has a zone of turbulent mixing of the combined liquid components. The turbulent mixing zone is preferably in a mixing chamber where the individual liquid components are combined into a single stream, but need not necessarily be. The zone of turbulence could for example be created by suitable turbulence-inducing structure downstream of the mixing chamber which structure acts on the combined flow inducing turbulence therein and enhance the mixing of the liquid components within the mixing head or applicator.

Preferably, the zone of turbulent mixing is created in a mixing chamber by constructing the chamber and fluid supply channels communicating therewith so that there is apposite mixing of the fluid flows in the mixing chamber. By "apposite mixing" is intended that the direction of flow of each fluid into the mixing chamber shall be such that there is substantial opposition of one flow to another so as to cause turbulent mixing.

A potential drawback of such enhanced mixing is that coagulation of the active components may be accelerated, leading to clogging from solids deposited within the mixing head's fluid passageways. To overcome difficulties with clogging, the invention preferably also provides clearing means to remove the deposited solids or to dislodge and remove deposited solids. Such clearing means preferably comprises retrograde suction applied to the combined liquid passageway to withdraw deposited solids, as for example described in co-pending application Ser. No. 08/838,078, and if desired, may also include means to dislodge deposited solids to facilitate their withdrawal, or removal by other means, such as will be described hereinafter.

The device shown schematically in FIGS. 2–? embodies such apposite mixing and solids clearing features of the invention. Referring to FIG. 2, a mixing head 50 comprises a U-shaped manifold 52, overlain by a generally rectangular shuttle valve 54 and a stop 56. U-shaped manifold 52 (shown in unbroken lines for clarity) has a central mixing chamber 58 and resiliently flexible tubular arms 59 whose walls can be pinched or otherwise pressed together to prevent the flow of liquid therethrough. Arms 59 are constructed and manufactured from a material selected to facilitate such pinching closure, at least in the vicinity of mixing chamber 58. Away from mixing chamber 58, arms 59 terminate in cups 60 that fit over the discharge nozzles of a pair of syringes 62, where tissue sealant components, or other materials, can be accommodated and furnished to mixing chamber 58. Cups 60 are internally fitted with seals 64 which provide a fluid-tight fit with the forward ends of syringes 38. Other, possibly continuous supply, sealant component feed means can be connected to cups 60, as will be apparent to those skilled in the art. The broken lines show an optional third syringe 62 and its accompanying fluid conduits which will be described more fully below.

Mixing chamber 58 is generally cylindrical and has a central mixing volume 66 into the sides of which manifold arms 59 open at ports 68. Ports 68 are diametrically opposed to one another, across the mixing volume 66, so that fluids, most probably liquids, fed simultaneously through manifold arms 59 will impinge directly upon each other. Downwardly, it communicates with a dispensing nozzle, or cannula, 70 into which fluids mixed in chamber 58 are discharged. Preferably, cannula 70 terminates in a discharge aperture 73 and has a tapering structure with a reducing cross-section from mixing chamber 58 to aperture 73 to facilitate retrograde withdrawal of debris by suction.

Prior to the present invention, it had been thought necessary that the sealant dispensing cannula should have a substantial length to keep the applicator and the user's hand well clear of the work surface at the site of application, for example, referencing a hand-held applicator having a length of the order of six inches (15 cm), a projecting length outside the applicator tip of about 1.5 or 2 (3.8 or 5) or more inches. However, pursuant to the present invention, it has now been discovered that the length of the mixed sealant conduit from mixing volume 66, at the point where the sealant components become mixed, to the point of discharge from the applicator should be as short as practicable to prevent clogging. Furthermore, it has surprisingly been found unnecessary to maintain substantial spacing between cannula 70's discharge aperture 73 and the user's hand (or cannula embracing finger), so that a short cannula, for example, projecting less than 1 inch (2.5 cm), preferably less than about 0.8 inches (1 cm) from the applicator body, can be used and is advantageous in enabling mixed fluids to be rapidly discharged from the applicator.

Toward the end of minimizing the the length of the mixed liquid pathway from point of mixing to point of exit from the device, it is desirable to locate mixing volume 66 closely to any external housing of the mixing head, for example as is achieved with the embodiment of applicator tip illustrated in FIGS. 7–19, notwithstanding the relative complexity of the internal components of the applicator tip depicted.

Preferably also, mixing volume 66 has a cross-sectional area in excess of the sum of the areas of arms 59 to provide an air volume to facilitate mixing, at least at the beginning of the applicator stroke wherein sealant components are driven from syringes 62 through arms 59 to an otherwise empty mixing chamber 66.

By employing an area for aperture 73 that is less than the combined cross-sectional areas of tubular arms 59 it is possible to build back pressure in cannula 70, and in mixing volume 66, which, combined with the free space therein and with the apposite positioning of the fluid streams as they are admitted to mixing volume 66, is helpful in promoting turbulent mixing and avoiding stratification of the fluid components in the dispensed fluid stream.

The schematic view of FIG. 3 illustrates the mixing principles of the invention as they apply to the mixing of sealant components, comprising fibrinogen and thrombin respectively, which are thoroughly mixed to provide an effective tissue sealant that is readily applied to a suction-prepared tissue surface.

Now thoroughly mixed, as they leave mixing chamber 66 and advance along cannula 70, the sealant components will begin to interact and cure. Accordingly, the length of cannula 70 should be selected according to the setup time of the sealant, taking into account the rate of transit of sealant mixture through cannula 70 to avoid clogging cannula 70. Cannula 70 can be provided in various lengths according to the particular purpose for which the applicator is to be employed so that where a short setup sealant is employed, for example a fibrin sealant using a thrombin component with an activity of the order of 100 IU, a particularly short cannula may be employed, whereas for a sealant with a longer setup time for example one provided with a thrombin component having a low activity of the order of 5 IU, a longer cannula 70 can be used.

Prior to the present invention, it had been thought necessary that the sealant dispensing cannula should have a substantial length to keep the applicator and the user's hand well clear of the work surface at the site of application, for example, referencing a hand-held applicator having a length of the order of six inches (15 cm), a projecting length outside the applicator tip of about 1.5 or 2 (3.8 or 5) or more inches. However, pursuant to the present invention, it has now been discovered that the length of the mixed sealant conduit from mixing volume 66, at the point where the sealant components become mixed, to the point of discharge from the applicator should be as short as practicable to prevent clogging. Furthermore, it has surprisingly been found unnecessary to maintain substantial spacing between cannula 70's discharge aperture 73 and the user's hand (or cannula embracing finger), so that a short cannula, for example, projecting less than 1 inch (2.5 cm), preferably less than about 0.8 inches (1 cm) from the applicator body, can be used and is advantageous in enabling mixed fluids to be rapidly discharged from the applicator.

Toward the end of minimizing the mixed liquid pathway from point of mixing to point of exit from the device, it is desirable to locate mixing volume 66 closely to any external housing of the mixing head, for example as is achieved with the embodiment of applicator tip illustrated in FIGS. 7–19, notwithstanding the relative complexity of the internal components of the applicator tip depicted.

One or more flanges, such as circumferential flange 71, or other suitable structure, can be provided to enable cannula 70 to be located and held in mating engagement with mixing chamber 58 by suitable support structure (not shown). Cannula 70 and mixing chamber 58 are canted downwardly and forwardly to facilitate application of the sealant, or other mixture of working fluids. Upwardly, mixing chamber 58 is slidingly engaged by shuttle valve 54 which rides on chamber 58 to control admission of suction thereto.

Stops 56 are located adjacent arms 59, as close as is practical to mixing chamber 58. Shuttle valve 54 comprises a rectangular body 72, from the rearward end of which extend elongated actuator members 74 having cam surfaces, the details of which are not here shown, but which can be used to drive the shuttle valve 54 back and forth in a forward then a rearward direction. Shuttle valve 54 has a central opening 76 to communicate with mixing volume 66 when the valve is in a forwardly advanced position, as shown in FIG. 5. When not forwardly advanced, shuttle valve 54 seals off the upper side of mixing volume 66. Clamping blades 78 depend downwardly from valve body 72 and cooperate with stops 56 on each side of mixing chamber 58 to clamp each manifold arm 59 individually between a clamping blade 78 and a stop 56 thereby to close the arm 59 against the flow of liquid as the shuttle valve 54 advances to its forward position.

The described components can all be manufactured from a suitable injection-moldable polymeric or plastics material, or the like, as will be known to those skilled in the art, provided that manifold arms 59 are sufficiently deformable and resilient to make a good closing seal when firmly clamped between clamping blade 78 and stop 56. Preferably, mixing chamber 58 has at least some limited resilient deformability, whereby the clamping of manifold arms 59, closely adjacent to mixing chamber 58, acts upon deposited solids in or near mixing chamber 58 to dislodge them facilitating their removal from the mixing head. Liquid in manifold arms 59 acts hydraulically in response to the squeezing pressure of clamping blades 78.

Such resilient deformability, as a characteristic of the material of manifold 52, is beneficial not only to permit proper closure, sealing and resilient re-opening of tubular arms 59 when engaged by clamping blades 78, but also as a characteristic of seals 64, to enhance their effectiveness, of the mixing chamber 58 to facilitate dislodgement of undesired solid deposits and to facilitate sealing engagement of mixing chamber 58 with shuttle valve 54 and dispensing cannula 70.

If suction is employed, (as it is in the preferred embodiments herein) to prepare, clean-up or manipulate the work surface, and it is desired to apply suction simultaneously with the tissue sealant, then suction can be applied through central opening 76, connecting with a suction conduit having an aspiration nozzle, or second cannula, terminating in an output aperture adjacent to that of dispensing cannula 70. Such suction-applying structure is not shown here, but an embodiment thereof is described in detail below in connection with FIGS. 7–20 and suitable implementations thereof depicting a complete suction conduit from source to the surface are also described in parent applications Ser. Nos. 08/838,078 and 08/839,614. It will be understood to that such parent applications also describe and disclose suitable embodiments of manually powered drive mechanisms and operating controls permitting delivery of sealant components and application of suction.

Suction clearing of any solids coagulating in the mixed liquid pathway is assisted by avoiding tortuous configurations of the mixed liquid pathway, by providing reducing cross-sectional area in the downstream direction, and by providing the mixed liquid pathway with smooth walls, preferably fabricated of a non-sticking material.

In use, an operator urges a manual actuator to drive sealant components through syringes 62 into manifold 52 where the components travel along arms 59 and emerge from ports 68 into mixing volume 66. As shown in FIG. 3, the alignment of ports 68 and arms 59 is selected so that the jets emerging from arms 59 into mixing volume 66 impinge directly upon one another, creating a zone of substantial turbulence in mixing volume 66 where the liquids are brought into intimate contact with one another and thus become thoroughly mixed. Such head-on impingement of the flows may be termed "apposite mixing". While a diametrically aligned apposition of the two liquid flows is preferential for more effective mixing, useful, albeit inferior mixing, can be obtained employing different alignments, for example with an included angle between the directions of flow at the point of mixing no less than 120°, preferably no less than 150°, rather than the preferred 180°, provided that substantial laminar flow through dispensing cannula 70 is prevented.

The efficacy of mixing, and thence the acceptability of any particular structural variation, can be determined by means of a simple test such as the use of blue and yellow colored liquid components, as described in connection with the prior art device shown in FIG. 1. A uniformly green product should be consistently dispensed from dispensing cannula 70.

A suction control valve is coupled with shuttle valve 54 whereby actuation of the suction control valve by the operator moves shuttle valve 54 forwardly from the position shown in FIG. 4 until central opening 76 registers with mixing volume 66, as shown in FIG. 5. The applied suction clears mixing volume 66 and dispensing cannula 70 of residual mixed sealant components, deposited solids and other debris. As shuttle valve 54 approaches the suction registration position of FIG. 5, clamping blades 78 engage resilient manifold arms 59 closely adjacent mixing chamber 68, compressing the arms 59 against stops 56 and closing them provide flow of flow of liquid sealant component therethrough. At the same time residual solids or debris adjacent ports 68 may be dislodged, squeezed or otherwise forced away from ports 68 into the upward suction stream in mixing volume 66, to be withdrawn from the device.

Preferably, the suction control valve and shuttle valve 54 are biased to return to the position shown in FIGS. 2 and 4, for example by being spring-loaded, enabling an operator to release the suction control and re-commence application of sealant. Such suction clearing means provides a simple and easy method of clearing the mixed liquid conduit.

An alternative construction of clearing means is shown in FIG. 6 which illustrates a modified dispensing cannula 75 which extends upwardly into mixing volume 66 where it has a sleeve portion 80 which is a close fit in mixing volume 66, providing a liner for mixing chamber 68. Openings are provided in sleeve portion 18 in registration with ports 68 to admit liquid components into mixing volume 66. Sleeve portion 80 of dispensing cannula 75 can be a press fit or snap fit in mixing volume 66 or otherwise can be releasably secured to mixing chamber 58 or to housing structure that effectively locates sleeve portion 80 in mixing volume 66. The modfied cannula 75 shown can be disposable, (although there are drawbacks associated with using disposable components with fast curing sealants, which are described below), but is also useful where the sealant components has a short setup time and clogging problems occur that are not resolved by the use of suction clearing. Also, cannula 75 can assist in dislodgement of any solid deposits in the vicinity of ports 68, when it is removed as its sleeve portion 80 exerts a mechanical disrupting action on any such deposits.

Such a dispensing cannula can be embodied in disposable form being readily removed, discarded and replaced with a new cannula at desired intervals, for example for each new patient, or procedure. Clogging resulting from the deposit of solids generated by reaction of the sealant components with one another and thus will only manifest itself as a problem in locations within the mixing head where the sealant components contact one another. Effectively this should be only at ports 68 and points downstream thereof. Accordingly, use of such a cannula can eliminate the need for suction to clear the mixed fluid conduits that are subject to clogging, as any contaminating debris in the conduit will be removed with the cannula and discarded. This capability may be valuable where suction is not readily available, for example in field conditions. However, one drawback to disposability is that sealant components are lost, and being valuable, wiht 1998 costs of the order of $100 per ml in the United States, such losses significant. Furthermore cannula or cannula-and-liner disposability is not an effective solution to clogging problems with a fast curing sealantwhich may clog in less than a minute during between the steps of a given procedure.

An unrelated benefit of cannula 75 is to provide a unique, non-adhesive surface material differing from the material of the individual fluid conduits, for example polytetrafluoroethylene for those fluid conduits that are exposed to mixed sealant.

If desired, disposable embodiments of dispensing cannula 70 can contain turbulence-creating structure such as fins, baffles or protrusions that so direct the liquids in the mixing volume or in the tubular cannula portion as to enhance turbulence and thence improve the mixing of the two or more liquid sealant components.

Such a removable cannula 70 can be economically fabricated as an inexpensive plastic molding and constitutes a simple and effective clearing means. While use of a removable cannula which effectively contains the complete mixed fluids conduit from a zone of mixing to the point of egress from the mixing head, can eliminate need for retrograde suction or other clearing means, if desired, suction clearing can also be used, either to clear the disposable cannula during use, or to clear mixing volume 66 with dispensing cannula 70 removed, or both. FIG. 6 illustrates how mixing chamber 58 can be modified by closing off the upward side of mixing volume 66. Shuttle valve 54 can also be simplified, if suction clearing is not employed, being constructed simply to operate clamping blades 78.

However, the value of suction for preparing the tissue surface and for removing excess adhesive calls for its use in many applications, so that suction will usually be readily available for the described clearing functions of the invention and its use is desirable.

The third syringe 62A, shown in broken lines in FIG. 2, can be positioned between, or beneath and between, the two syringes 62 and, as indicated, manifold 52 can be provided with a third arm 59A and cup 60A to communicate with syringe 62A. Such is preferably operated in harness with syringes 62 to deliver liquid therefrom simultaneously with the delivery of fluids from syringes 62. However, third syringe 62A may have a different geometry, to provide a different flow rate, if desired.

Figure 7:
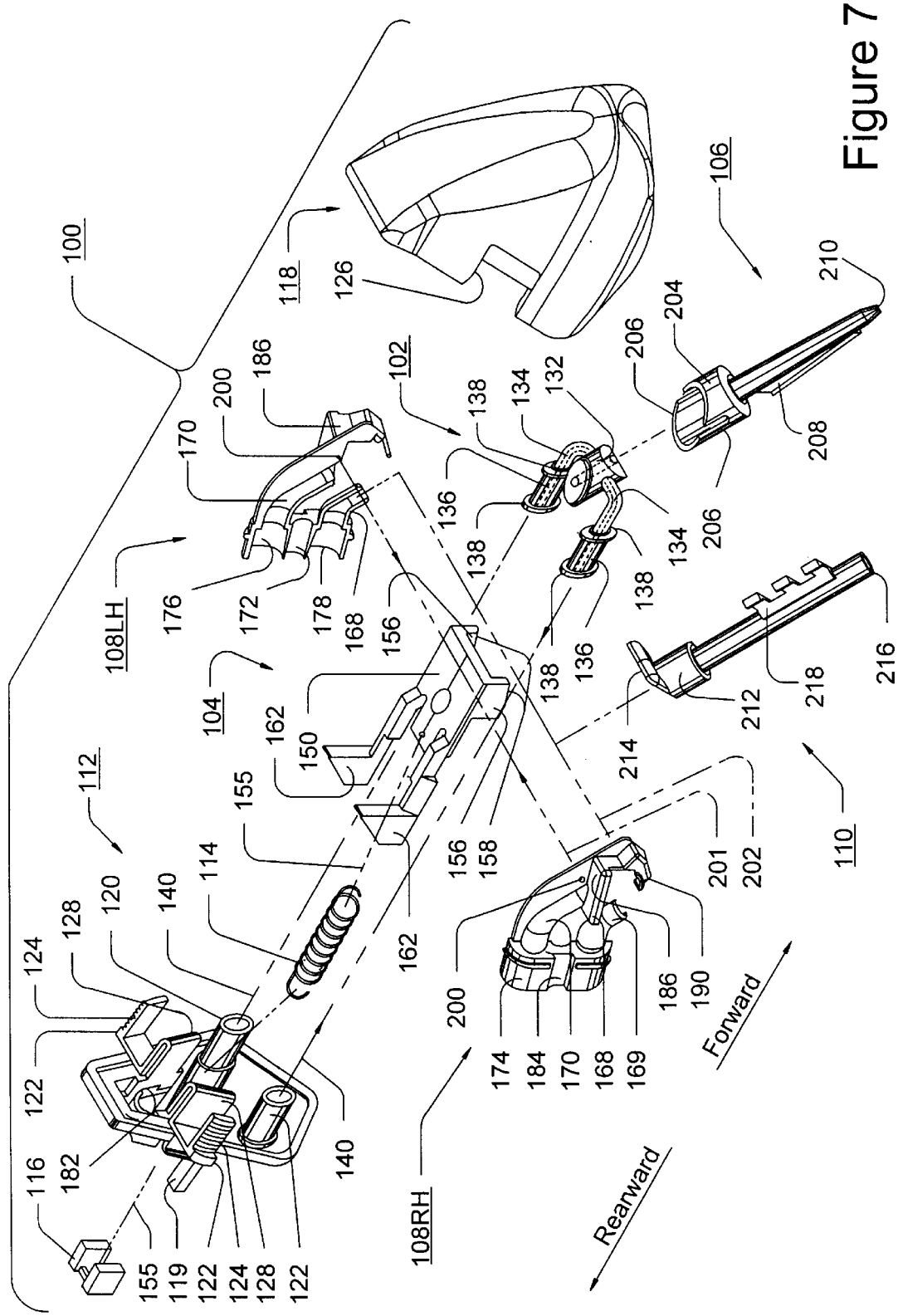
FIG. 7 is an exploded view of a novel applicator tip for a tissue sealant applicator which comprises a further embodiment of mixing head according to the invention.

Third syringe 62A can accommodate, or provide, a third sealant component or an additive useful at the work site, for example a therapeutic composition. Preferably, the dispositions of port 68A and arm 59A are such that the liquid flow from syringe 62A into mixing volume 66 is apposite to the flows of one or both of the liquid components from syringes 62, whereby mixing of all three components is facilitated or enhanced. For example, the three flows may be directed to a common point of convergence, as shown in FIG. 7. The efficacy of mixing of 3 sealant components can also be determined using colored liquids. However, rather than trying to select three different colors that will mix to produce a suitably indicative end product, it is preferred again to use blue and yellow liquids, with a clear liquid in the third syringe 62 or 62A and perform the test three times, rotating the colors between the syringes to show satisfactory mixing in pairs. If every pair mixes well, it is reasonable to assume that all three liquids will blend well. If one or more liquids has significant viscosity, the test liquid should be made comparably viscous, e.g. by using a transparent thickening agent such as carbopol or agar.

The tissue sealant applicator tip embodiment incorporating a mixing head shown in FIGS. 7–19 is a more detailed embodiment of the invention which embodiment includes most of the features shown in the embodiment of FIGS. 2–6 and is suitable for manufacturing from injection molded plastics components. As will be described, several of the parts of the mixing head shown in FIGS. 7–19 embodying similar construction and functionality to the components of the embodiment of shown in FIGS. 2–6.

Many individual structural features of the components of the applicator tip can be seen from the exploded view of FIG. 7, while FIGS. 8–14 and 18–19 show additional structural features and relationships of the internal components and FIGS. 14–17 show the overall external appearance of the applicator tip.

Referring to FIG. 7, the mixing head 100, there shown in exploded view, comprises a U-shaped manifold 102, embodying features of manifold 52, a shuttle valve 104, embodying features of shuttle valve 54 and a dispensing cannula 106 embodying features of dispensing cannula 70. Additionally, mixing head 150 comprises an inner clamshell 108which supports manifold 102, shuttle valve 104 and dispensing cannula 106 in assembled configuration, and an aspiration cannula 110 which is similarly supported in assembled configuration with the foregoing parts by clamshell 108 where it connects with the suction conduit through the mixing head 150 and the applicator. Clamshell 108 has a left-hand half designated 108 LH and a right hand half designated 108 RH. The numeral "108" is used to reference the two halves conjointly.

In preferred embodiments, shuttle valve 104, dispensing cannula 106, aspiration cannula 110, clamshell 108, connecting plate 112 and an attractively styled tip housing 118 are essentially rigid, injection-molded components having limited resilience in their thinner sections. In contrast, manifold 102 is preferably fabricated from a distinctly elastomeric, resilient molding material so that, in a relaxed state, the tubular arms of manifold 102 unfold and extend in a straight line. Manifold 102 is preferably also transparent as are other liquid-contacting components, to permit limited inspection of the liquid conduits through the mixing head. A suitable material for manifold 102 is ?? while other, liquid contacting components are preferably fabricated of a polymeric plastics material such as polypropylene, or polytetrafluoroethylene, to resist adhesion by fibrin.

Connecting plate 112 mates with the assembled manifold 102 shuttle valve 104 and clamshell 108 and is provided with suitable structure on its rearward face to connect with an applicator body. A tension spring 114 connected to a bifurcated retainer block 116 on one side of connecting plate 112 and to the shuttle valve 104 on the other side of connecting plate 112 biases shuttle valve 104 in the rearward direction. An attractively styled tip housing 118 completes the mixing head assembly, fitting over manifold 102, clamshell 108 and shuttle valve 104 and snap fitting with connecting plate 112 to form an integral assembly from which dispensing cannula 106 and aspirator cannula 110 depend downwardly and forwardly toward a work surface.

Connecting plate 112 comprises a pair of forwardly extending sleeves 120 which are received over the forward ends of liquid component feed syringes such as syringes 62 (FIGS. 2–6), and above which are located a pair of S-shaped compression latches 122 having manually depressible ribbed outer tab portions 124. Tip housing 118 has cutouts 126 (one shown in FIG. 7) to accommodate latches 122 and is internally configured to be a snap fit over mounting plate 112, with the remaining components of the applicator tip mounted thereon (see FIG. 18).

Rearwardly, connecting plate 112 has a pair of flanged guide pegs 119 to stabilize the attachment of the applicator tip to an applicator body. Inner portions 128 of latches 122 provide resilience and enable guide pegs 119 to be securely engaged in an applicator body by a user compressing tabs 126 together with their thumb and forefinger.

Centrally, connecting plate 112 has an aperture 130 configured to receive and locate the forward end of clamshell 108. On its rearward surface connecting plate 112 is configured to receive and locate spring retainer 116. Manifold 102 comprises a central mixing chamber 132 from which extend tubular arms 134, which arms terminate in cylindrical cups 136, which cups 136 fit snugly within sleeves 122 of connecting plate 112 where they are located by external colors 138. Cups 136 are internally configured to be pressed into tight sealing engagement, when so mounted within sleeves 122, with the forward ends of sealant component syringes mounted in a mating applicator body, to receive liquid components therefrom. The interfitting relationship between cups 136 and sleeves 122 is indicated by broken lines 140.

Tubular arms 134 of manifold 102 are flexible and can readily be manipulated during assembly of the mixing head 100, to be turned from an unassembled, relaxed state, straight line configuration, as shown in FIG. 8, through 90 degrees to align each cup 136 with the syringes in the applicator body, along the rearward-forward direction shown, while the inward ends of arms 134 maintain an apposite alignment at the mixing chamber 132 to effect apposite, turbulent mixing of liquids conveyed through the arms 134. A cross-section through mixing chamber 132 and arms 134 is essentially similar to FIG. 3. Mixing volume 148 opens downwardly to a sealant discharge opening 149 which communicates with cannula 70, and upwardly to port 151 which communicates with a suction clearing conduit, to be described.

The flexibility of tubular arms 134 simplifies manufacure and provides considerable freedom of movement of the outward ends of cups 136, which facilitates assembly of mixing head 100, accommodates tolerances in other components and can also accommodate minor design variations in other components that may be required from time to time. Molding of the in-line relaxed state configuration (FIG. 8, broken lines) is considerably easier than would be the U-shaped assembled configuration which might have to be molded in two halves.

Mixing chamber 132 has a frusto-cylindrical shape with an upper surface 142 which is approximately horizontally disposed and bears a unitary upstanding sealing ring 144 which makes a substantially airtight seal with shuttle valve 104. Under surface 146 of mixing chamber 134 is perpendicular to the direction of extent of dispensing cannula 106 and enters into sealing engagement therewith for which purpose under surface 146 could be provided with a seal similar to seal 144, if desired. Internal passages in manifold 102 are shown in broken lines and provide a mixing volume 148 similar to mixing volume 66, FIG. 2.

Other minor structural features such as abutments will be apparent from the drawings, or can be added by those skilled in the art. While manifold 102 could be integrally constructed from a number of components, preferably and advantageously, it is a unitary structure. By incorporating a number of components into a single element, capable of injection molding fabrication, considerable economy of manufacture and reliability of operation is obtained. Of significant value is the fact that one element, manifold 102, provides multiple resilient seals for fluid tight engagement with four other components, namely two syringes, shuttle valve 104 and dispensing cannula 106. Seals that would otherwise be required if mixing chamber 132 and arms 134 were separate components are also eliminated. Manifold 102 also constitutes a useful service component that can readily be replaced.

Shuttle valve 104 comprises a generally rectangular body 150 having a central opening 152 and a small rearward opening 154 which is engaged by forward end of tension spring 114, as indicated by broken line 155. Spring 114, anchored by retainer block 116 engaging clamping plate 112, biases shuttle valve 104 rearwardly, causing valve 104 to return to its sealant dispensing position after it has been forwardly advanced to effect suction clearing of mixing volume 148 and dispensing cannula 106. Clamping blades 156 depend downwardly from the forward end of body 150, have a partially rectangular shape with their lowermost forward corners cut back to provide an inclined surface 158 to engage tubular arms 134 of manifold 102 closely adjacent mixing chamber 132, as shown in FIGS. 12–13. Elongated actuator members 160 extend rearwardly from rectangular body 150 and terminate in upstanding buttresses 162 which present upward facing cam surfaces 164 for engagment by manual actuation of the suction valve (not shown). Intermediately their lengths, actuator members 160 have guide portions 166 which engage and are guided by outer surfaces of clamshell 108.

Referring to clamshell 108, as shown in FIG. 10, it will be appreciated that the structural elements described are, for the most part, provided conjointly by structure from both halves only clamshell 108 LH and 108 RH. Thus, clamshell 108 comprises a suction aspiration conduit 168 in the lower half of the clamshell and a suction clearing conduit 170 in the upper half of the clamshell. Suction aspiration conduit 168 communicates with the suction valve (in the applicator body, not shown) and terminates in a port 169 which receives aspiration cannula 110, while suction clearing conduit 170 communicates suction from the suction valve to mixing chamber 148 and thence to dispensing cannula 106.

Intermediately of suction conduits 168 and 170, a short tubular opening 172 is provided to accommodate spring 114. The rearward end of clamshell 108 comprises a shroud 174 configured to be received through connecting plate 112 and to present aspiration and clearing suction ports 176 and 178 respectively for to communicate with the applicator's suction valve. Ribs 180 locate clamshell 108 against receiving structure 182 in mounting plate 112.

Externally, shroud 174 has a pair of right-section recesses 184 which engage with guide portions 166 of shuttle valve 104, positioning the valve as it moves back and forth. Centrally, clamshell 108 is formed with a horizontally disposed rectangular box portion 186 which accommodates rectangular body 150 of shuttle valve 104 for sliding movement therein. Laterally of box portion 186, each half of clamshell 108 is formed with an opening 188, configured with an arcuate rest 190 to accommodate a respective tubular resilient arm 134 of manifold 102 and shaped to permit a respective clamping blade 156, depending from forward portion of body 150 of shuttle valve 104, to engage the arm 134 pinching its walls together against rest 190 and preventing fluid flow therethrough.

Box portion 186 has an end wall 192 which extends across the full width of shuttle valve 104 and is engaged by an end face 194 on shuttle valve 104 to provide a positive limit to forward movement of the shuttle valve. The geometry is selected such that this limit is reached at a point which protects tubular arms 134 from undue compression, yet permits effective closure of the arms by clamping blades 156 to stop fluid flow therethrough.

A hook-like structure at the forward end of clamshell 108 has an opening 196 which receives and supports dispensing cannula 106, and laterally thereof has extensions 198 that support arcuate seats 190 for manifold arms 134. When its two halves 108LH and 108RH are assembled together, using one or more press fit studs such as 200, and as indicated by broken line 201, clamshell 108 is designed to be a sturdy component which supports and holds shuttle valve 104 and manifold 102 together with cannulas 106 and 110 in a proper working relationship for assembly to connecting plate 112. Broken line 202 indicates the assembly point of cannulae 106 and 108 with clamshell 108.

Figure 18:
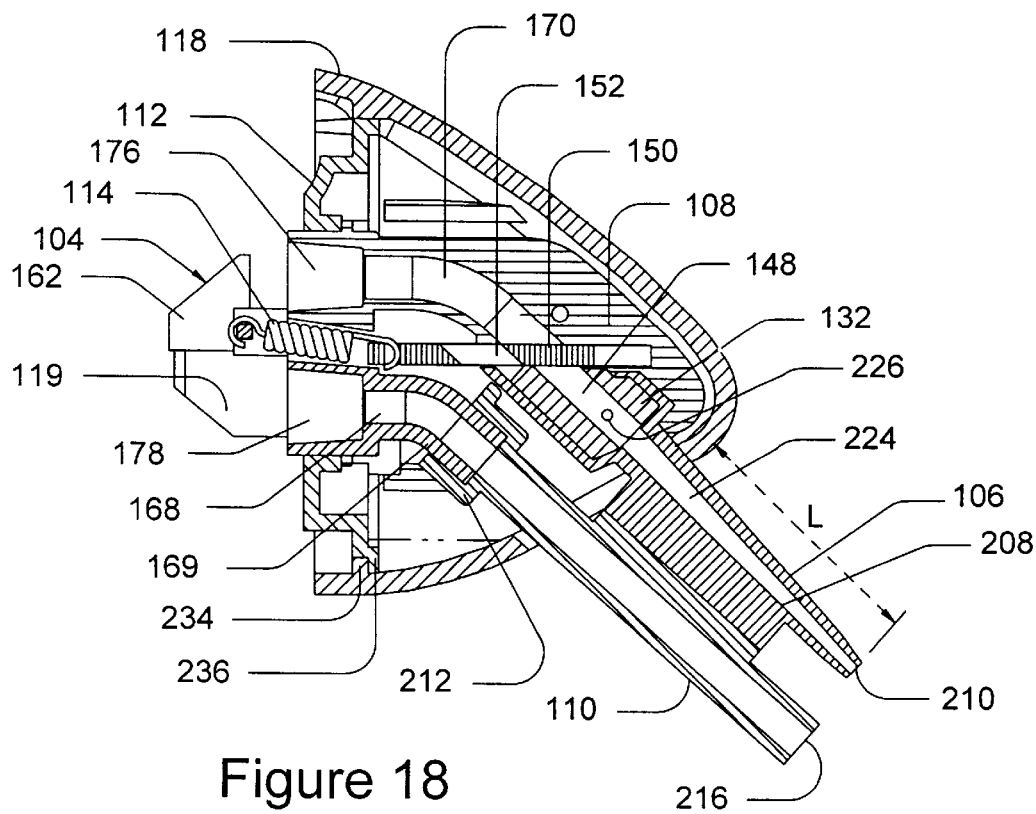
FIG. 18 is a section on the line 18—18 of FIG. 16, with the shuttle valve in a rearward position.
Figure 19:
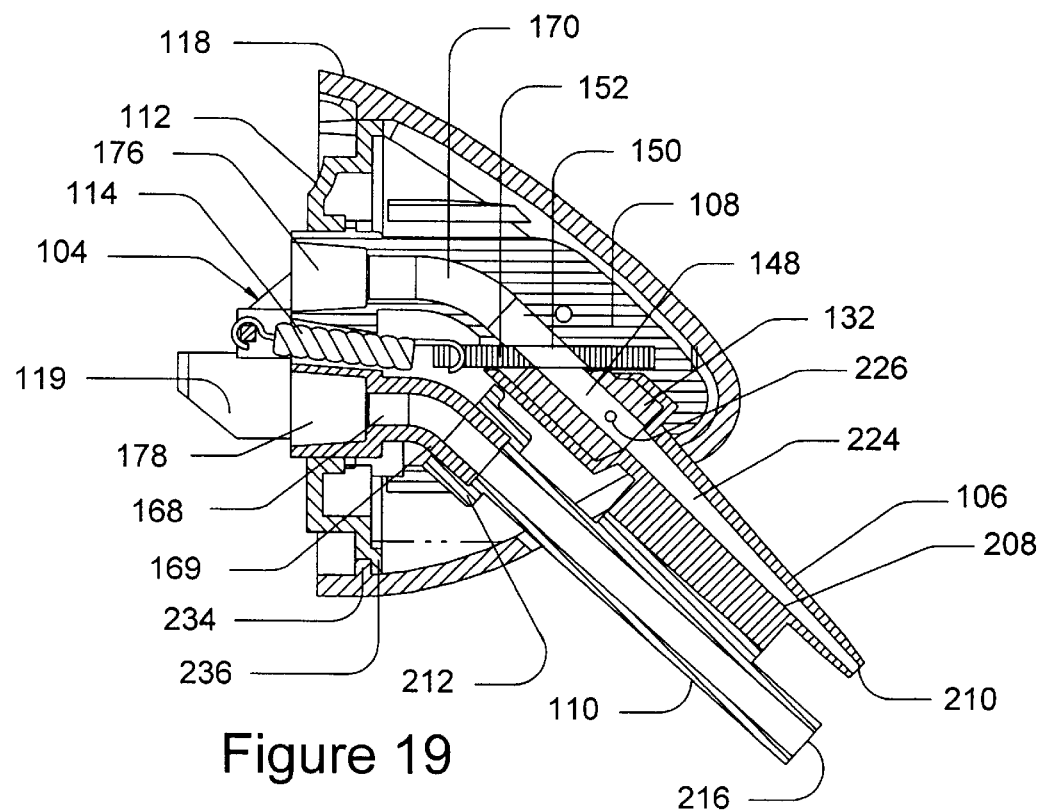
FIG. 19 is view similar to FIG. 18 with the shuttle valve in a forward position.

Spring 114 holds these components in place in relation to clamping plate 112 while tip housing 118 is internally configured so that when it is snap fitted to connecting plate 112 all components are properly located and securely held in position (FIGS. 18–19).

Referring to FIGS. 11–13, when manifold 102 is assembled with clamshell 108, it is precisely located therein with manifold arms 134 supported on arcuate rests 190 and extending outwardly through openings 188 to be folded rearwardly for engagement over syringes such as 62 when the applicator tip is attached to an applicator body. Shuttle valve 104 is free shuttle back and forth with its body 150 and depending clamping blades 156 located substantially within the clamshell 108, subject to the to the rearward biasing action of spring 114. In FIG. 11, shuttle valve 104 is shown retracted somewhat rearwardly from its normal rearward position to expose the structure of the top of mixing chamber 132 and seal 144. In the normal rearward position of shuttle valve 104, FIG. 18, body portion 150 overlies the top of mixing chamber 132 and makes an air-tight seal with seal 144, preventing upward discharge of sealant fluids.

It is of course desirable to avoid contamination of the underside of shuttle valve body 150 with sealant fluids which might result in shuttle valve 104 seizing up and jamming the applicator. To this end, mixing chamber 132 has a significant extent above arms 134 to reduce the probability that back splash within chamber 132 will strike body 150 and provide an air cushion to deter such contamination and help smooth the output of sealant from dispensing cannula 106. A further function of resilient seal 144 is to wipe the under surface of body 150 to remove any liquid or solid deposits therefrom, which can then be aspirated from mixing volume 148, in suction clearing mode.

Referring to FIGS. 12–13, in FIG. 12 shuttle valve 104 has begun its forward movement in response to user actuation of the suction valve and inclined surface 158 of clamping blade 156 is tangentially engaging an upper surface of tubular arm 134. As shuttle valve 104 advances into the fully forward position of FIG. 13, tubular arm 134 is progressively compressed in a controlled and graduated manner until end face 194 of valve 104 engages end wall 192 of clamshell 108.

At this point tubular arm 134 is closed to the passage of fluid therethrough but, by proper choice of the geometry is not unduly stressed. Rather than being absorbed as a crushing force on tubular arm 134, any excess closing load is applied directly to end wall 192 and the load is spread over a much more substantial area that is provided by a blade 156 engaging, 134.

As described hereinabove, the geometry is also preferably selected so that blades 156 engage arms 134 closely beside mixing chamber 132 to help dislodge any clogging solids that congregate in the vicinity of mixing chamber 132's inflow ports. Dislodging forces are transmitted hydraulically from the point of closure of tubular arms 134 through the sealant component liquid in the arm to the obstruction, if present, as each arm is squeezed by clamping blade 156.

Dispensing cannula 106 comprises an upper cup-shaped portion 204 which fits closely around the mixing chamber 132 and has side slots 206 to accommodate arms 134. As stated above, cannula 106 is constructed of a relatively rigid material so that cup portion 204 can locate and position the cannula in clamshell 108 and also support and locate mixing chamber 132 within clamshell 108. Such support is needed to provide dimensional stability, noting that manifold 102 is formed of a relatively resilient material. Downwardly of cup portion 204 cannula 106 is provided with an alignment bar 208 extending along a significant portion of the length of the cannula, below which the cannula terminates in a dispensing aperture 210. Cannula 106 has an internal flow path which decreases in cross-sectional area toward aperture 210, as will be described in more detail in connection with FIGS. 18 and 19.

Cannula 110 has a collar 212 at its upper end which press fits on to suction clearing conduit port 169 and engages tightly therewith. Collar 212 has a projecting flange 214 that engages and supports cup-shape portion 204 of cannula 106. Aspiration cannula 110 terminates in an aspiration aperture 216 and intermediate its length has a set of claw-like projections 218 to engage and cooperate with alignment bar 208 to provide suitable relative positioning of cannulas 106 and 110.

As best shown in FIGS. 14–17, tip housing 126, tip housing 118 neatly accommodates the assembly of clamshell 108, shuttle valve 104, manifold 102 and connecting plate 112 with cannulas 106 and 110 projecting from the housing 118 through openings 220 and 222.

Tip housing 118 is attractively and aesthetically styled and provides a convenient, ergonomically designed device which can be readily assembled with a sealant applicator such as is disclosed in the parent applications and when assembled therewith can be precisely and dextrously manipulated to apply suction and sealant to tissue surfaces, for example to perform, or in the course of performance, of a surgical operation.

In a preferred embodiment, the complete applicator, with an applicator tip as shown, can comfortably be held between the forefinger, index finger and thumb, much like a writing instrument enabling a user to take advantage of their natural precision motor actions developed for writing or drawing, to dispense sealant skillfully.

Connecting plate 112 comprises a pair of forwardly extending sleeves 120 which are received over the forward ends of liquid component feed syringes such as syringes 62 (FIGS. 2–6), and above which are located a pair of S-shaped compression latches 122 having manually depressible ribbed outer tab portions 124. Tip housing 118 has cutouts 126 (one shown in FIG. 7) to accommodate latches 122 and is internally configured to be a snap fit over mounting plate 112, with the remaining components of the applicator tip mounted thereon (see FIG. 18).

Rearwardly, connecting plate 112 has a pair of flanged guide pegs 119 to stabilize the attachment of the applicator tip to an applicator body. Inner portions 128 of latches 122 provide resilience and enable guide pegs 119 to be securely engaged in an applicator body by a user compressing tabs 126 together with their thumb and forefinger.

NEW TEXT

FIGS. 18–19 show clearly the respective rearward and forward positions of shuttle valve 104. In FIG. 18 body portion 150 of shuttle valve 104 closes the upper side of mixing volume 148 and the buttress portions 162 of the valve can be seen projecting rearwardly from plate 112, while in FIG. 19 shuttle valve 104 has moved forwardly, bringing opening 152 into registration with mixing volume 148 to apply suction to clear the mixing volume and cannula 106 (arms 134 being closed by clamping blades 156). The extension of return spring 114 may also be seen in FIG. 19.

The internal configurations of cannula 106 and mixing volume 148, which provide the mixed fluids exit pathway from the applicator tip and which open rearwardly into conduit 170, to provide a suction pathway for retrograde clearing of the cannula, can best be seen by referring to FIGS. 18, and 19. The interior walls of cannula 106 and mixing volume 148 preferably smooth, polished and formed of a material resistant to adhesion, for example, cannula 106 can be formed of a highly polished rigid polypropylene or polytetrafluoroethylene.

To reduce the probability of clogging, the length L of cannula 106 is kept as short as is practicable and is consistent with ergonomic and surgical requirements. Thus, referring to the case of a hand-held applicator intended for dispensing tissue sealant, cannula 106 should project a sufficient distance from tip housing 118 to allow the housing tip 118 to be properly gripped by the user's fingers or fingers and thumb, while still providing a working length of cannula 106 with which to address tissue surfaces of various configurations and accessibility. A suitable value of L, consistent with efficient manipulation of the applicator in the manner described below, lies within the range of from about 0.6 to about 1.2 inches (1.5 to 3 cm), preferably about 0.75 inches (close to 2 cm).

Tip housing 118 is designed to facilitate support of the applicator in a user's hand while gripping and manipulating cannulas 106 and 110, which are effectively rigidly interconnected by bar 208 and projections ?. For this purpose, tip housing 118 has features such as a convergent nose portion 228, with a downwardly inclined, laterally curved upper face 230 which can be held under a user's forefinger, and a small flattened underface 231 which can rest on a user's index finger. Coupled with the forward location of openings 220 and 222, these features enable the complete applicator to be readily gripped like a pen, or other writing or drawing instrument, by supporting the housing tip 118 on the index finger with cannulas 106 and 110 projecting over and resting on the index finger while the forefinger extends across the top of the applicator gripping surface 230 to provide control while the body of the applicator extends between the thumb and forefinger and the thumb is left free tooperate necessary controls such as a fluid dispensing control and a suction control ergonomically located on top of the applicator, for example, as shown in the parent applications.

Thus held, the complete applicator (see the parent applications) can extend across the side of the hand with a suction supply line draped across one side of the hand or the other and has a surprisingly well-balanced feel so that it is comfortable and convenient to use and can be operated with precision. Other ways of manipulating the applicator will be apparent to those skilled in the art.

As previously discussed, it is desirable to provide rapid mixing and a short mixed fluids pathway out of the applicator, to prevent clogging, or undue viscosity build-up. As shown, cannula 106's internal fluid passage, here designated 224, tapers toward dispensing aperture 210, while mixing chamber 132 is disposed closely adjacent to tip housing 118 to shorten the length of the mixed fluids pathway which can be defined to begin at fluid admission port 226 where manifold arm 134 (not visible in FIGS. 18–19) opens into mixing chamber 148. The relative dimensions of the several fluid conduits that lead into and comprise the mixed fluid pathway can be selected to enhance rapid mixing and rapid discharge of the mixed sealant components.

Referring to the cross-sectional areas of the various conduits and ports, (which will determine the fluid flow rate for a given drive pressure and fluid viscosity), the cross-sectional area of mixing volume 148 substantially exceeds the combined areas of arms 134 at ports 226, being, for example, at least twice as large, or preferably three or more times as large as the port areas, to provide, at least at the beginning of a fluid dispensing stroke, free space in mixing volume 148 for hydraulic-pneumatic turbulent mixing of the incoming fluid sealant components.

Cannula 106's internal passage area 224, at its upstream end, is somewhat less than that of mixing volume 148, to ensure that no obstruction to retrograde suctional clearing can occur at the boundary between the two, yet, preferably also substantially exceeds the combined port areas. Passage 148 tapers downwardly to aperture 216, where it has an area which is preferably less than the combined areas of ports 168, being for example comparable with that of a single port 168, to provide back pressure to promote continued turbulent mixing in mixing volume 148 and the upper end of cannula 106.

As may further best be seen in FIGS. 18–19, tip housing 118 has an internal lip 234 at its lower periphery which latches in a mating recess 236 in the lower periphery of connecting plate 112. Tip housing 118 may be assembled with the remaining applicator tip components, after they have been assembled with connecting plate 112, by passing cannulas 106, 110 through openings 220, 222, latching lip 234 into recess 236 and snapping the top of the tip housing over the top of the connecting plate.

Figure 20:
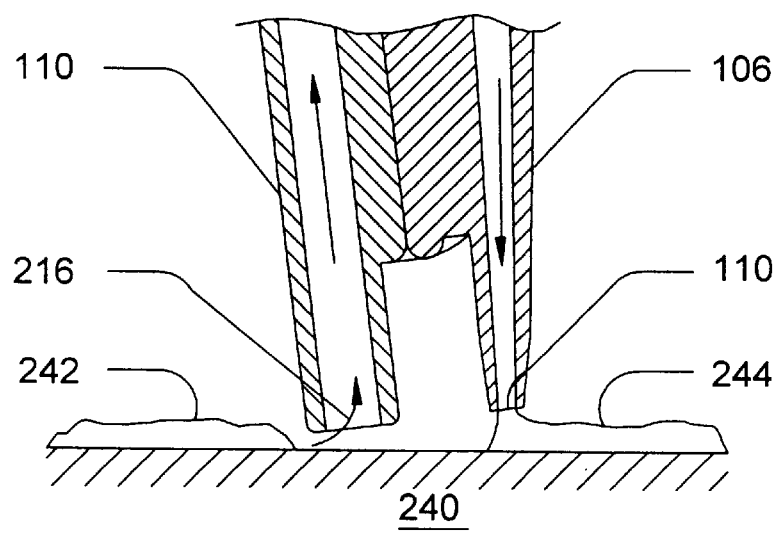
FIG. 20 is a schematic view of the simultaneous application of suction and sealant to a tissue surface.
Figure 21:
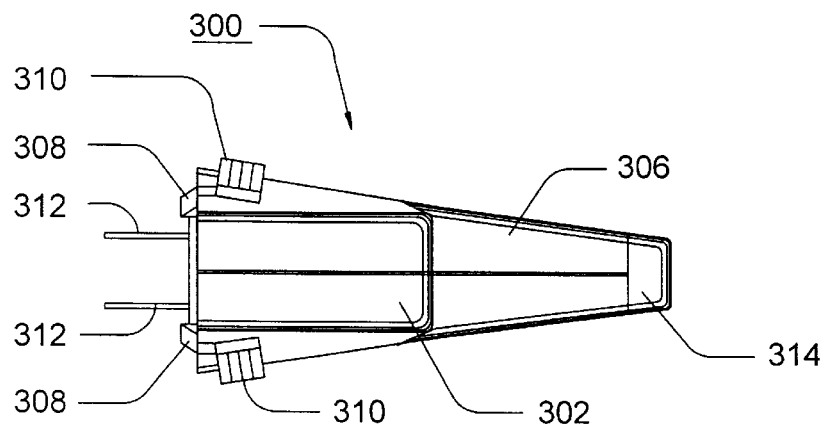
FIG. 21 is a top plan view of a spray head applicator tip according to another aspect of the invention.
Figure 23:
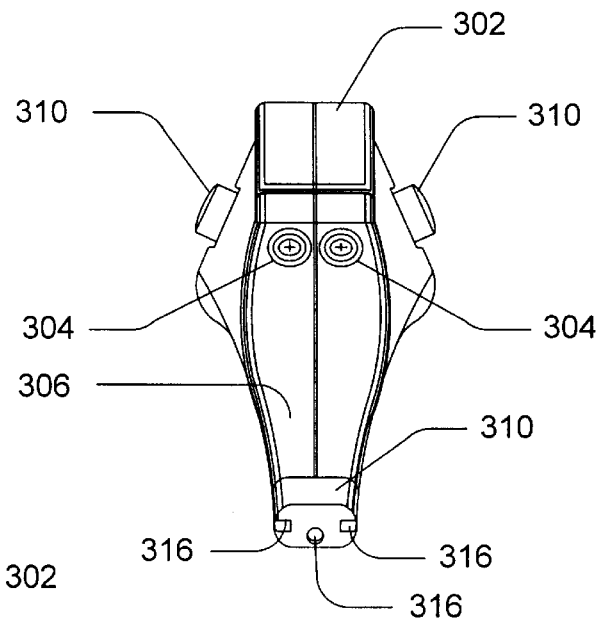
FIG. 23 is a front elevational view of the spray head shown in FIG. 21.
Figure 22:
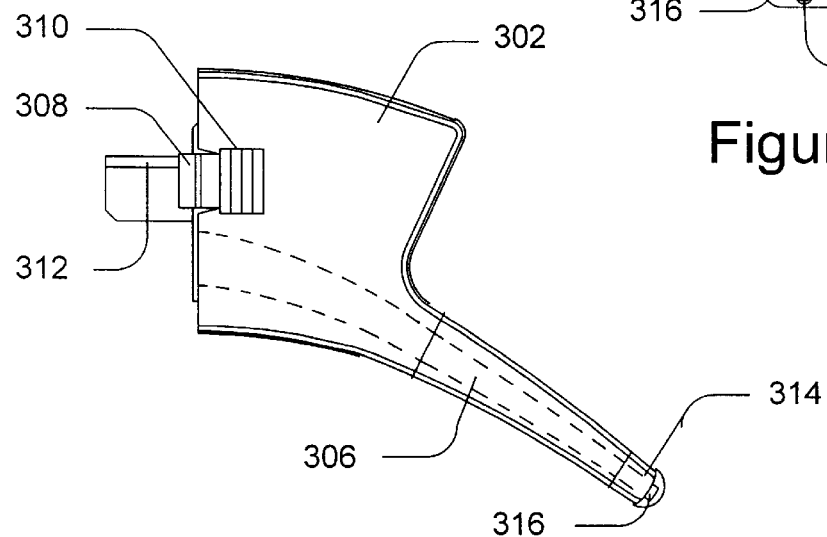
FIG. 22 is a side elevational view of the spray head shown in FIG. 21.

The applicator tip described with reference to FIGS. 7–19 can readily be assembled with an applicator body, gripped, manipulated and manually actuated to dispense desired patterns of thoroughly mixed adhesive with sufficient accuracy for many surgical purposes, including drops or spot patterns, droplets, beads and continuous line patterns. As shown in FIG. 20, the positioning, disposition and proximity of suction aperture 216 permits tissue 240 to be cleaned of fluids 242, or other debris, and dried prior to application of sealant 244 by drawing the applicator toward the user, while also removing any excess sealant that comes within range of suction aperture 216.

A suitable applicator body for assembly with the droplet applicator tip illustrated in FIGS. 6–19 is shown in FIGS. 25 and 27 with a spray head attached, the spray head shown comprising an embodiment of a further invention herein. In a preferred embodiment, the droplet applicator tip, an extended reach version thereof, for example as shown in FIGS. 18A–C of parent application Ser. No. 08/ (case GE 400), and a spray head such as that shown in FIGS. 21–27, described below, are interchangeably fittable (by the user) not only to the barrel style of applicator shown, but also to a pistol grip applicator such as shown in the parent applications.

Comparative tests were conducted to compare the performance of a fibrin sealant applicator according to the invention employing a droplet head with apposite mixing substanatially as described with reference to FIGS. 7–19, "the inventive applicator" with two commercially available applicators, namely an applicator sold under the trademark DUOFLO by Haemedics Corp. and an applicator sold under the trademark FIBRIJECT by Micromedics Corp.

Two fibrin sealant components were used namely a bovine- sourced cryoprecipitate, BioSurgical Corp., fibrin sealant component 1, and topical thrombin in 40 mM $CaCl_2$, fibrin sealant component 2, JMI, Inc.

Test subjects were rabbits, the kidneys and spleen of each of which were exposed and incisions of controlled length and depth were made. Fibrin sealant was then applied by one of three sealant applicators. The time to hemostasis was recorded.

The following procedures were used:
Kidneys
1. Expose the left kidney via a midline abdominal incision.
2. Carefully dissect kidney free from any adherent tissue or fat.
3. Elevate kidney and place gauze underneath, spreading out to isolate organ from surronding anatomic features.
4. Clamp a hemostat to a # 10 scalpel blade so that 3 mm of the tip is exposed.
5. Place a scale longitudinally along the upper lateral edge of the kidney and make an incision 20 mm long.
6. Once bleeding has begun, lightly dab incision with gauze and immediately apply fibrin sealant with test applicator.
7. Record time until essentially all bleeding has ceased (slight oozing). Continue to record time until complete hemostasis occurs. Discontinue all time measurements after 10 minutes is still bleeding.
8. Repeat steps 5 through 7 for the lower lateral edge of the left kidney.
9. Steps 5 through 7 may be repeated for the ventral side of the kidney if more data points are needed.
10. Repeat steps 2 through 7 for the right kidney.

Spleen
1. Expose the spleen via the same midline excision made for the kidneys
2. Carefully dissect spleen free from any adherent tissue or fat.
3. Elevate spleen and place gauze underneath, spreading out to isolate organ from surrounding anatomic features.
4. Clamp a hemostat to a # 10 scalpel blade so that 3 mm of the tip is exposed.
5. Place a scale lengthwise along the lateral end of the spleen and make an incision 20 mm long.
6. Once bleeding has begun, lightly dab incision with gauze and immediately apply fibrin sealant with test applicator.
7. Record time until essentially all bleeding has ceased (slight oozing). Continue to record time until complete has hemostasis occurs. Discontinue all time measurements after 10 minutes if still bleeding.
8. Move scale at least 20 mm proximally from the first incision and repeat steps 5 through 7.
9. Continue to make incisions and measurements by moving continually proximal from the previous incision as long as there is sufficient length remaining to do so.
10. Once all incisions have been made, the subject may then be sacrificed by standard means.

The performance of each tested applicator was assessed using the following criteria:
1. Time to near complete hemostasis (slight oozing).
2. Time to complete hemostasis.
3. Percentage of sites with hemostasis as a function of time within 10 minutes.
4. Quantity of sealant delivered.

The results set forth in Table 1 below were obtained:

TABLE 1

COMPARATIVE TEST RESULTS
Hemostasis in Rabbits

|  | Kidney 1 | Kidney 2 | Spleen |
| --- | --- | --- | --- |
| Rabbit 1 Haemedics Applicator | 20 seconds | 25 seconds (2 applications) had to clean out passages total $2^{nd}$ for all 3 incisions used | 1 minute 48 seconds (2 applications) |

TABLE 1-continued

COMPARATIVE TEST RESULTS
Hemostasis in Rabbits

|  | Kidney 1 | Kidney 2 | Spleen |
|---|---|---|---|
| Rabbit 2 Haemedics Applicator | 48 seconds (3 applications) | 12 seconds (1 applications) | 50 seconds (3 applications) |
| Rabbit 3 Inventive Applicator | <1 second 1 ml | <1 second 0.6 ml | <1 second .1 ml *no bleeding through sealant very white in color |
| Rabbit 4 Inventive Applicator | 20 seconds (poor applications) 0.6 ml | 25 seconds 0.6 ml | <1 Small leak on top due to poor coverage. Sealant application sealed instantly |
| Rabbit 5 Micromedics Applicator | 25 seconds | 1 minute 13 seconds Haemedics 2 ml | >3 minutes |
| Rabbit 6 | 1 minute 25 seconds Haemedics Applicator | 1 minute 30 seconds Inventive Applicator | 60 seconds Inventive Applicator |

Referring to FIGS. 21–26, a spray head 300 according to another apect of the invention comprises a skull portion 302 carrying externally (FIGS. 21–23) two side-by-side forwardly directed spray nozzles 304 to supply individual patterns of fluid sealant components, (a third, or even a fourth, nozzle could be added, if desired for therapeutic, indicator, conditioner, or other agents), a forwardly projecting, extensible nose 306 to apply suction, a rearwardly disposed connecting plate 308 and latches 310. Nozzles 304 can discharge relatively wide, overlapping patterns of sealant components, which mix on contact with a work surface (or in the air), enabling a multi-component sealant to be applied in a relatively wide swathe, for example to control extended area oozing tissues in surgery.

Connecting plate 308 carries guide tabs 312 which are received into an applicator body and is generally similar to connnecting plate 112, FIGS. 7–19, but is simplified by the absence of a shuttle valve, since spray head 300, because it does not internally mix the sealant fluids, does not require clearing.

Nose 306 has a laterally extended width and terminates in an extensible end portion 314 having multiple suction apertures 316 enabling suction to be applied across a wide swathe, mimicking the sealant swathe. Thus, by drawing the applicator, equipped with spray head 300, toward themselves, the user can prepare a wide are of tissue with suction in advance of application of sealant.

Figure 24:
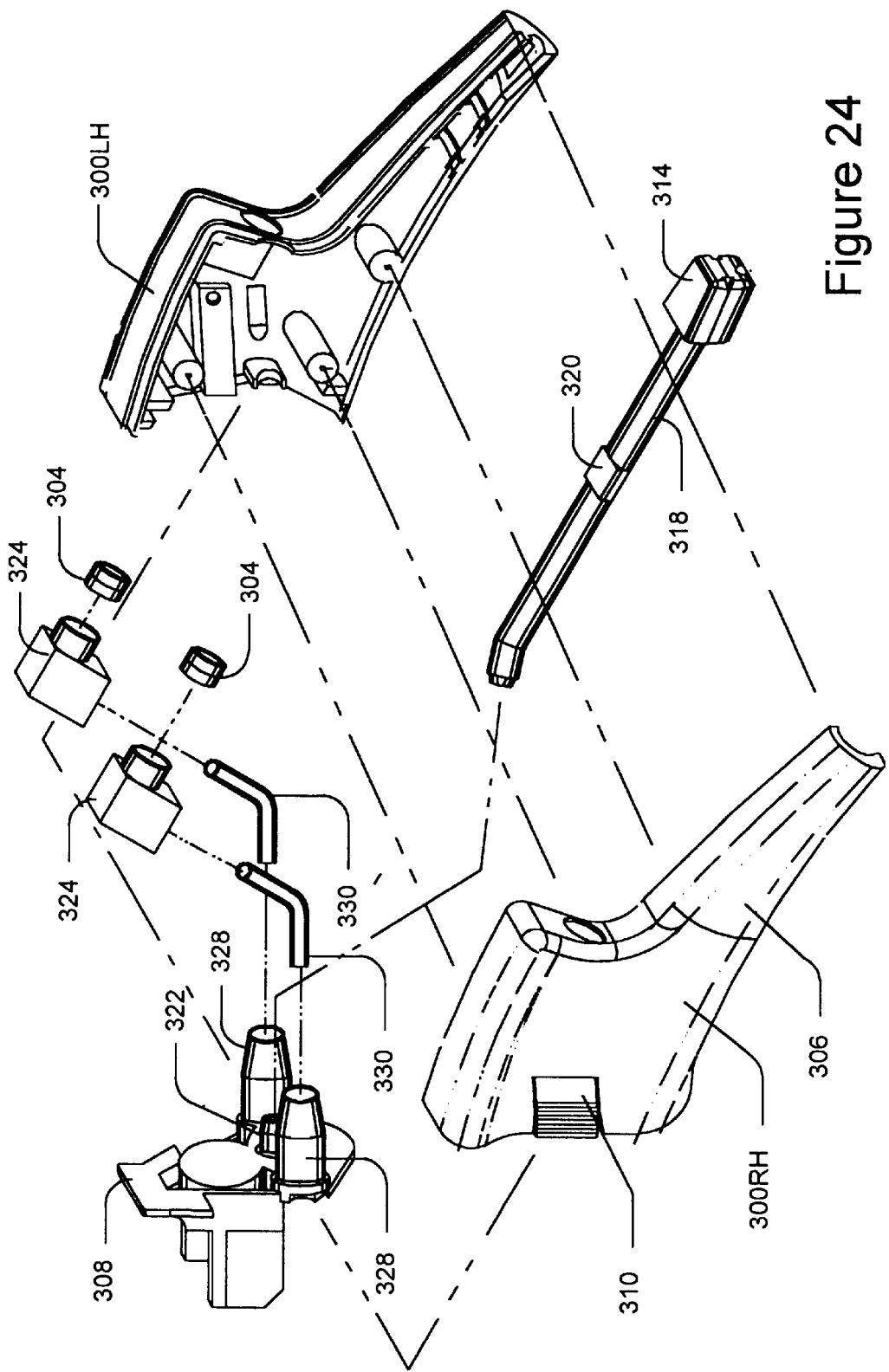
FIG. 24 is an exploded perspective view of the spray head shown in FIG. 21.

Referring to the exploded view of FIG. 24, in which component assembly is indicated by broken lines, spray head 300 is molded in complementary interlocking righthand and lefthand halves 300RH and 300LHand internally, has a telescopic suction tube 318 having a stop 320 which bears nose end portion 314, in extensible manner, and connects to a port 322 on connecting plate 308 to receive suction.

Poppet valves 324 mount in rectangular cutouts 326 in spray head 300, carry spray nozzles 304, and connect with two sealant component sleeves 328 on connecting plate 308 via two elbow conduits 330. Sleeves 328 receive sealant fluids from syringes such as 62 (FIG. 2) supported in an applicator body 3?? (FIGS. 25–26). Poppet valves 324 comprise spring-biased valve elements, described in more detail hereinbelow, which control sealant fluid flow out of nozzles 304 to provide a clean discharge of spray and avoid leakage, runs or dribbles.

Referring to FIGS. 25–28, spray head 300 is shown assembled with an applicator body 332, details of which are described in the parent applications, which applicator body 332 can also be used with the droplet applicator head of FIGS. 7–19. Applicator body 332 comprises a suction port 334 connectable with a suction line, a depressible suction control valve 336, a depressible sealant fluid actuator trigger 338 and a manually retractable indicator bar 340 which can be used to draw fluid into syringes within the applicator to refill them from a filling tray such as that shown in the parent applications.

As shown in FIG. 25 the assembled spray applicator is designed to be held at an angle of the order of 30 degrees to the horizontal by a user with a fore finger above, and an index finger beneath skull portion 302, leaving the thumb free to operate actuator trigger 338 and suction control valve 336. Extensible nose 306 can be used as a probe or feeler gauge and can be drawn along a work surface 342, for example mammalian tissue to be treated, spacing spray nozzles 304 a suitable distance from the work surface 342.

The user operates suction control valve 336 as nose 306 travels across work surface 342, as desired, to aspirate fluids and other debris through suction apertures 316 in end portion 314 across a relatively wide swathe. When sealant spray is desired, actuator trigger 338 is depressed, repeatedly if necessary, until sufficient pressure is built up in the fluid delivery system to open poppet valve 324 and release a conical pattern 344 of sprayed fluid from each poppet valve 324.

The angle of the applicator to the work surface 342 means that an elliptical pattern 346 of spray is deposited on the work surface, as shown in idealized manner in FIG. 26. Spray nozzles 304 are oriented so that their spray patterns overlap as completely as practicable at the intended work surface distance, and as indicated in FIG. 26, this overlap can be, at least theoretically, very nearly complete. The sealant components are thus separated from one another until after they leave the spray head, thereby avoiding any possible problems of clogging within the spray head. By suitable selection of spray nozzle 304, and valve 324, fine sprays can be obtained ensuring that with the excellent overlap illustrated in FIG. 26, thorough mixing of the sealant components takes at the work surface, providing excellent efficacy of sealant application enabling, for example, rapid hemostasis, control of oozing or such desired surgical result.

As shown in FIGS. 27 and 28 the spray pattern can be enlarged and controlled by extending end portion 314, giving nose 306 a greater length and, as it were, lengthening the feeler gauge to distance the spray nozzles 304 from the work surface. If desired, detents can be provided to enable end portion 314 to be locked in any one of a variety of positions, or friction control may be used to make its extension continuously selectable.

Reducing pressure on trigger 338 causes poppet valve 324 to close, terminating the spray cleanly, without dribbles. With this system, employing fluid reservoirs in the applicator, such as syringes of 62 enables sprayed sealant to be delivered continuously for a substantial period of time, as determined by the capacity of a syringe. Use of the poppet valve system is particularly helpful when one or more of the sprayed components is significantly viscous. Thus the poppet valve can be selected to have a suitable release pressure such as to ensure that the viscous fluid is properly discharged, without premature dribbling. To this end, it will be understood that the poppet valves and nozzles used in a given spray head may differ according to the liquid to be sprayed, for example, using a less viscous liquid on one side and a more viscous liquid on the other.

Three or more liquids can be sprayed, from three or more spray nozzles 304, if desired, for example two sealant components and a therapeutic agent.

Figure 29:
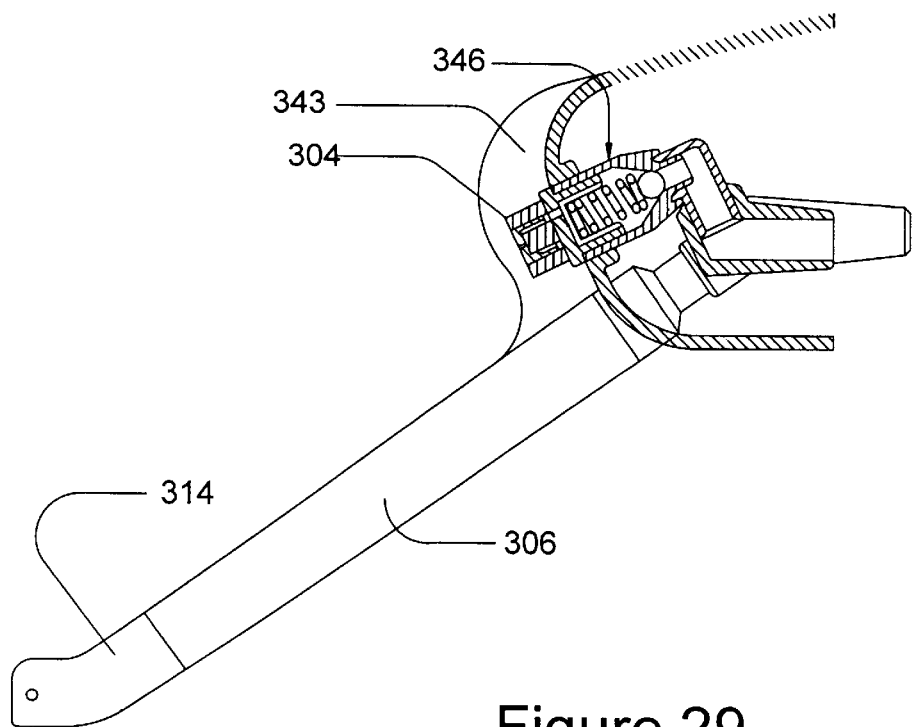
FIG. 29 is a left side elevational view of another embodiment of spray head according to this aspect of the invention, cutaway to show, in section, one construction of poppet valve for controlling spray output.
Figure 30:
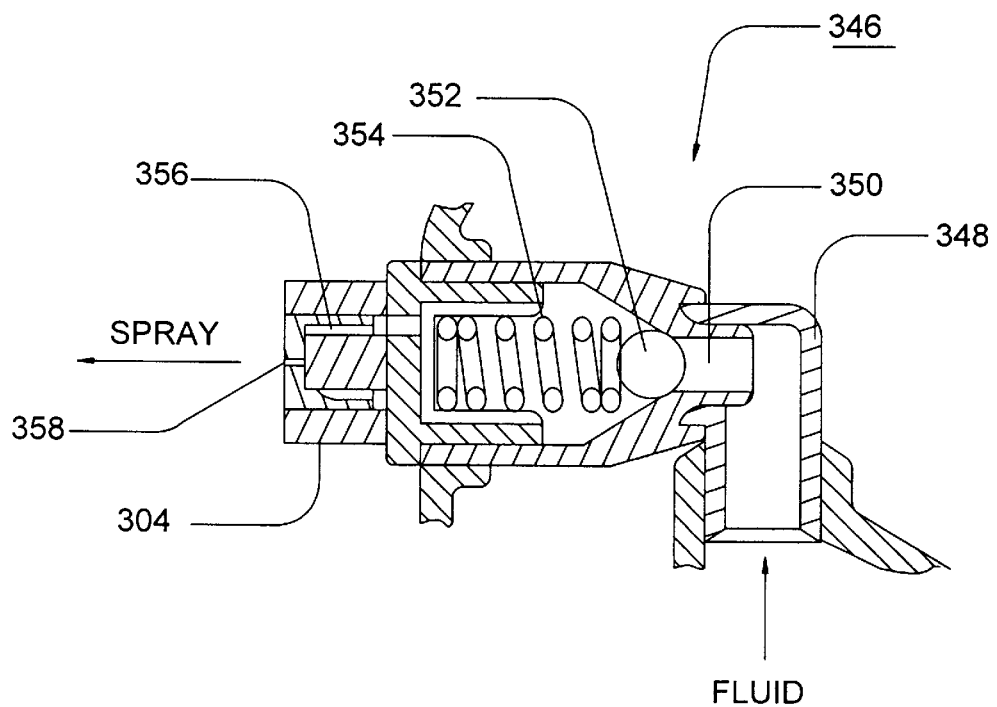
FIG. 30 is an enlarged view of the poppet valve section shown in FIG. 29.

The alternative construction of spray head shown in FIG. 29 employs a separator 342 between the spray nozzles 304 (one shown), to avoid cross-contamination, and uses a spring-biased ball-type poppet valve 346 to control discharge of fluid from the spray head, as shown in FIG. 30. With suitable modification, the poppet valve shown can serve as valve 324 for the spray head of FIGS. 25–28.

Referring to FIG. 30, a sealant fluid is delivered through a conduit 348 to port 350 which is closed by ball 352 held in sealing engagement therewith by compression spring 354. When the user builds sufficient pressure in passage 348 to overcome the action of spring 354, by depressing actuator trigger 338, ball 352 moves away from port 352 allowing fluid to pass through passage 356 to spray nozzle 304 where it is discharged from orifice 358.

Figure 31:
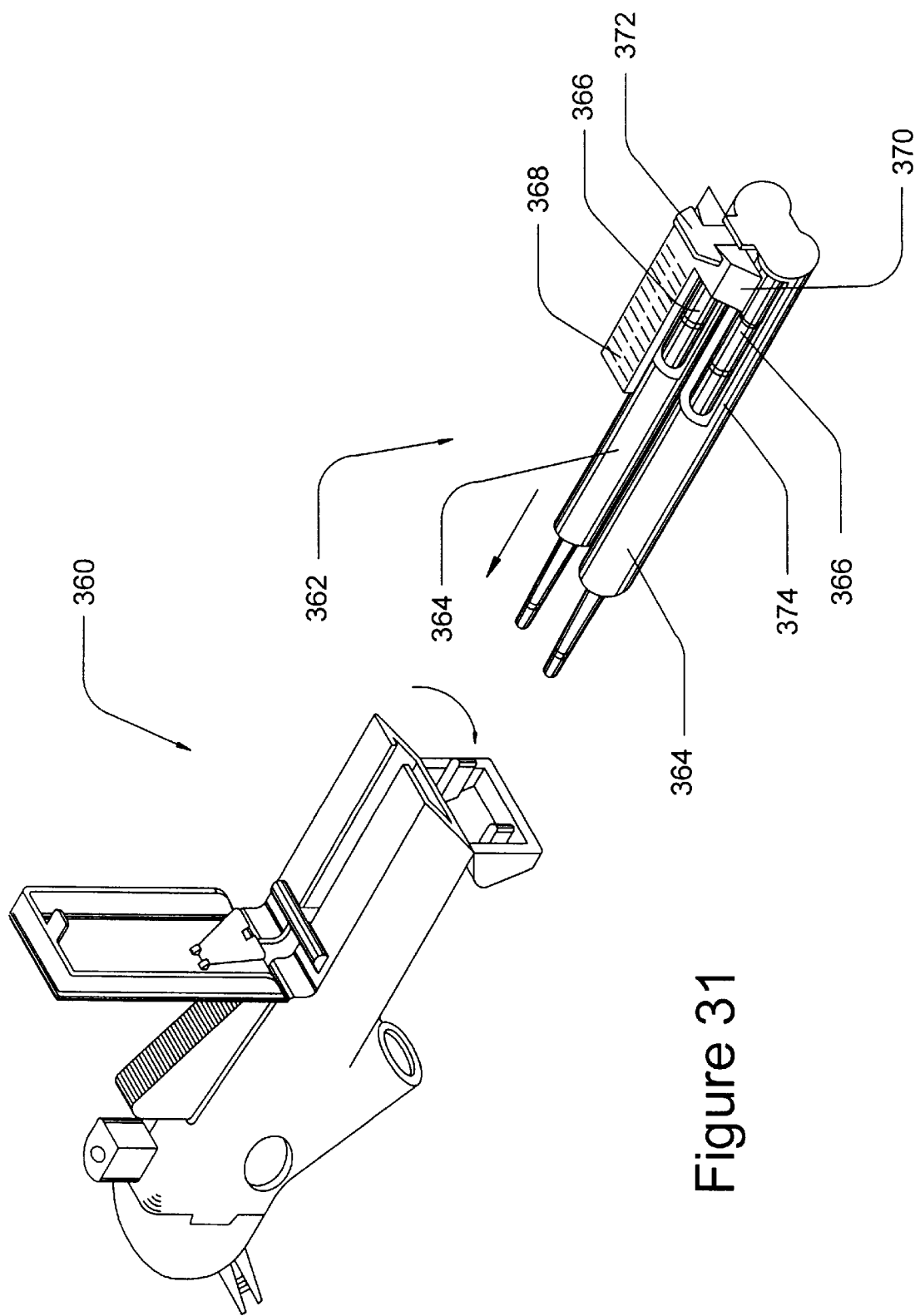
FIG. 31 is a perspective view of a modified construction of applicator body.

The embodiment of applicator shown in FIG. 31 is designed for the commercial supply of dual charges of sealant components, e.g. a fibrinogen containing component and a thrombin containing component as an integral disposable cartridge which can readily be removed from and replaced in the applicator and is not intended to be refilled, as are syringes 62. For this purpose, the rearward end of an applicator body 360 such as applicator body 332 is openable to receive a replaceable cartridge 362 which in addition to two sterilized and sealed syringe containers 364 comprises such of the functional elements of the applicator drive mechanism as are necessary to provide for replaceability in the stressful, time-sensitive environment of an operating room, for example, as shown, plungers 366, a rack 368, a coupling 370 between the two and a pull tab 372, which components are fixedly mounted in a tray 374. Containers 364 have removable tips 376 that are removed prior to insertion of the cartridge or breached by internal structure in the applicator (not shown). Optionally, containers 364 could be separable from cartridge 362, to be also replaceable, but if so, they should preferably be paired and keyed to ensure that the user can quickly insert the right combination of components in the applicator.

While illustrative embodiments of the invention have been described above, it is, of course, understood that various modifications will be apparent to those of ordinary skill in the art. Such modifications are within the spirit and scope of the invention, which is limited and defined only by the appended claims.

What is claimed is:

1. A manually actuated sealant applicator for dispensing a mixed output of at least two liquid sealant components, the sealant components being capable, when mixed together, of generating a solid sealant product, the applicator comprising:
   a) a mixing volume for mixing said at least two liquid sealant components;
   b) at least two liquid sealant component delivery passages to deliver respective flows of the sealant components separately to the mixing volume each flow having a sealant component input direction wherein the sealant component input directions are disposed at an included angle of at least 120 degrees, optionally at least 150 degrees, and are disposed to cause the sealant component flows to impinge one upon the other in the mixing volume thereby to cause turbulent flow of the liquid sealant components to enhance mixing of the components; and
   c) a clearing mechanism capable of providing a clearing force to act on and clear undesired solid sealant product from the mixing volume.

2. A sealant applicator according to claim 1 wherein the sealant flow input directions are directly opposed to one another.

3. A sealant applicator according to claim 1 being capable of repeated operation in a cycle comprising dispensing of mixed sealant component, solids formation and operation of the clearing mechanism to clear the formed solids from the mixing volume, wherein the sealant components are again dispensed through the mixing volume after clearing the mixing volume, in operating cycles subsequent to a first cycle.

4. A sealant applicator according to claim 1 comprising a dispensing tube connecting with the mixing volume to receive a stream of mixed fluid sealant from the mixing volume in a mixed sealant output direction and to dispense the mixed stream at a location displaced away from the mixing volume.

5. A sealant applicator according to claim 1 having an angle of at least 60 degrees between each sealant component input direction and the mixed sealant output direction.

6. A sealant applicator according to claim 1 wherein the mixing volume has a cross-sectional area in the vicinity of the delivery passages being greater than the sum of the cross-sectional areas of the delivery passages, said cross-sectional areas being determined transversely to the direction of fluid flow, to facilitate mixing of the fluid components.

7. A sealant applicator according to claim 1 comprising a sealant component flow control valve actuated by the clearing mechanism to close the sealant delivery passages and prevent flow of the sealant components into the mixing volume during clearing.

8. A sealant applicator according to claim 7 wherein the mixing volume comprises a clearing port for removal of undesired solids by the clearing mechanism and the sealant component flow control valve is operative to close the clearing port when sealant is dispensed and to open the clearing port when the clearing mechanism is operative.

9. A sealant applicator according to claim 1 comprising a dispensing tube connecting with the mixing volume to receive a stream of mixed fluid sealant from the mixing volume in a mixed sealant output direction and to dispense the mixed stream at a location displaced away from the mixing volume wherein the sealant flow input directions are directly opposed to one another and wherein the mixed sealant output direction is approximately perpendicular to each sealant flow input direction.

10. A sealant applicator according to claim 9 wherein the mixing volume has a cross-sectional area in the vicinity of the delivery passages being greater than the sum of the cross-sectional areas of the delivery passages, said cross-sectional areas being determined transversely to the direction of fluid flow, to facilitate mixing of the fluid components.

11. A sealant applicator according to claim 10 comprising a sealant component flow control valve actuated by the clearing mechanism to close the sealant delivery passages and prevent flow of the sealant components into the mixing volume during clearing wherein the mixing volume comprises a clearing port for removal of undesired solids by the clearing mechanism and the sealant component flow control valve is operative to close the clearing port when sealant is dispensed and to open the clearing port when the clearing mechanism is operative.

12. A sealant applicator according to claim 1 comprising at least two reservoirs, one for each respective sealant component, each sealant component delivery passage connecting with a respective one of the reservoirs to receive a sealant component therefrom.

13. A sealant applicator according to claim 12 for dispensing a fibrin sealant wherein one of the at least two reservoirs is charged with fibrinogen and another is charged with a fibrinogen activator, the fibrinogen activator optionally being thrombin.

14. A sealant applicator according to claim 1 wherein the clearing mechanism operates to apply retrograde suction to act on and clear undesired sealant product from the mixing volume.

15. A sealant applicator according to claim 1 comprising a passageway for dispensing the mixed output from the mixing chamber, the passageway comprising a tapered tube and nozzle.

16. A sealant applicator according to claim 1 wherein each delivery passage comprises a resiliently flexible tube, having walls that can be pinched closed to prevent flow of fluid therethrough.

17. A sealant applicator according to claim 16 comprising a one-piece manifold, the manifold being formed of a resilient material and comprising the mixing chamber and the resiliently flexible tubes.

18. A sealant applicator according to claim 17 wherein each resiliently flexible tube has a cup-shaped fitting at one end, each of the fittings being secured to a source of the fluid sealant components.

19. A sealant applicator according to claim 18 wherein the cup-shaped fittings further comprise internal seals providing a fluid-tight attachment to each source of the fluid sealant components.

* * * * *